(12) United States Patent
Stahmann et al.

(10) Patent No.: US 12,383,201 B2
(45) Date of Patent: Aug. 12, 2025

(54) MEDICAL SYSTEM FOR TREATING A LEFT ATRIAL APPENDAGE

(71) Applicant: BOSTON SCIENTIFIC SCIMED, INC., Maple Grove, MN (US)

(72) Inventors: Jeffrey E. Stahmann, Ramsey, MN (US); Bin Mi, Arden Hills, MN (US); Keith R. Maile, New Brighton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 671 days.

(21) Appl. No.: 17/591,101

(22) Filed: Feb. 2, 2022

(65) Prior Publication Data

US 2022/0240856 A1     Aug. 4, 2022

Related U.S. Application Data

(60) Provisional application No. 63/145,144, filed on Feb. 3, 2021.

(51) Int. Cl.
*A61B 5/00* (2006.01)
*A61B 5/0215* (2006.01)
*A61F 2/24* (2006.01)

(52) U.S. Cl.
CPC ............ *A61B 5/686* (2013.01); *A61B 5/0004* (2013.01); *A61B 5/0215* (2013.01); *A61F 2/243* (2013.01);
(Continued)

(58) Field of Classification Search
None
See application file for complete search history.

(56) References Cited

U.S. PATENT DOCUMENTS

| 178,283 A | 6/1876 | French |
| 1,967,318 A | 7/1934 | Monahan |

(Continued)

FOREIGN PATENT DOCUMENTS

| CN | 1399571 A | 2/2003 |
| CN | 202143640 U | 2/2012 |

(Continued)

OTHER PUBLICATIONS

International Search Report and Written Opinion dated Aug. 3, 2004 for International Application No. PCT/US2004/008109.
(Continued)

*Primary Examiner* — John R Downey
*Assistant Examiner* — Anant A Gupta
(74) *Attorney, Agent, or Firm* — Seager, Tufte & Wickhem LLP

(57) ABSTRACT

A medical system for monitoring a left atrial pressure in a heart of a patient may include an implantable device including an expandable framework and a first sensor secured to the expandable framework and an external component configured to communicate wirelessly with the implantable device. The first sensor may be configured to detect a first measurement. The first sensor may be a pressure sensor and the first measurement may be the left atrial pressure. The implantable device or the external component may include a processor configured to create a first trend for the first measurement. The processor may be configured to use the first trend to modify the first measurement prior to outputting a corrected result.

4 Claims, 14 Drawing Sheets

(52) U.S. Cl.
CPC ... *A61B 2562/0247* (2013.01); *A61B 2562/16* (2013.01)

(56) References Cited

U.S. PATENT DOCUMENTS

| | | |
|---|---|---|
| 3,402,710 A | 9/1968 | Paleschuck |
| 3,540,431 A | 11/1970 | Mobin-Uddin |
| 3,557,794 A | 1/1971 | Van Patten |
| 3,638,652 A | 2/1972 | Kelley |
| 3,811,449 A | 5/1974 | Gravlee et al. |
| 3,844,302 A | 10/1974 | Klein |
| 3,874,388 A | 4/1975 | King et al. |
| 4,007,743 A | 2/1977 | Blake |
| 4,108,420 A | 8/1978 | West et al. |
| 4,175,545 A | 11/1979 | Termanini |
| 4,309,776 A | 1/1982 | Berguer |
| 4,341,218 A | 7/1982 | Ü |
| 4,364,392 A | 12/1982 | Strother et al. |
| 4,425,908 A | 1/1984 | Simon |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand et al. |
| 4,665,906 A | 5/1987 | Jervis |
| 4,681,588 A | 7/1987 | Ketharanathan et al. |
| 4,710,192 A | 12/1987 | Liotta et al. |
| 4,718,417 A | 1/1988 | Kittrell et al. |
| 4,759,348 A | 7/1988 | Cawood et al. |
| 4,781,177 A | 11/1988 | Lebigot |
| 4,793,348 A | 12/1988 | Palmaz |
| 4,827,907 A | 5/1989 | Tashiro |
| 4,832,055 A | 5/1989 | Palestrant |
| 4,873,978 A | 10/1989 | Ginsburg |
| 4,917,089 A | 4/1990 | Sideris |
| 4,921,484 A | 5/1990 | Hillstead |
| 4,960,412 A | 10/1990 | Fink |
| 4,966,150 A | 10/1990 | Etienne et al. |
| 4,998,972 A | 3/1991 | Chin et al. |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,418 A | 4/1992 | Lefebvre |
| 5,108,420 A | 4/1992 | Marks |
| 5,108,474 A | 4/1992 | Riedy et al. |
| 5,116,360 A | 5/1992 | Pinchuk et al. |
| 5,122,136 A | 6/1992 | Guglielmi et al. |
| 5,171,259 A | 12/1992 | Inoue |
| 5,171,383 A | 12/1992 | Sagaye et al. |
| 5,176,692 A | 1/1993 | Wilk et al. |
| 5,192,301 A | 3/1993 | Kamiya et al. |
| 5,211,658 A | 5/1993 | Clouse |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,279,539 A | 1/1994 | Bohan et al. |
| 5,284,488 A | 2/1994 | Sideris |
| 5,304,184 A | 4/1994 | Hathaway et al. |
| 5,306,234 A | 4/1994 | Johnson |
| 5,312,341 A | 5/1994 | Turi |
| 5,329,942 A | 7/1994 | Gunther et al. |
| 5,334,217 A | 8/1994 | Das |
| 5,344,439 A | 9/1994 | Otten |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,331 A | 3/1995 | Himpens et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,427,119 A | 6/1995 | Swartz et al. |
| 5,433,727 A | 7/1995 | Sideris |
| 5,443,454 A | 8/1995 | Tanabe et al. |
| 5,443,478 A | 8/1995 | Purdy et al. |
| 5,451,235 A | 9/1995 | Lock et al. |
| 5,454,365 A | 10/1995 | Bonutti |
| 5,464,408 A | 11/1995 | Duc |
| 5,469,867 A | 11/1995 | Schmitt |
| 5,490,856 A | 2/1996 | Person et al. |
| 5,497,774 A | 3/1996 | Swartz et al. |
| 5,499,975 A | 3/1996 | Cope et al. |
| 5,499,995 A | 3/1996 | Teirstein |
| 5,522,790 A | 6/1996 | Voll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,558,093 A | 9/1996 | Pomeranz et al. |
| 5,558,652 A | 9/1996 | Henke |
| 5,569,204 A | 10/1996 | Cramer et al. |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,345 A | 10/1997 | Euteneuer |
| 5,681,347 A | 10/1997 | Cathcart et al. |
| 5,683,411 A | 11/1997 | Kavteladze et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,704,910 A | 1/1998 | Humes |
| 5,709,224 A | 1/1998 | Behl et al. |
| 5,709,704 A | 1/1998 | Nott et al. |
| 5,709,707 A | 1/1998 | Lock et al. |
| 5,722,400 A | 3/1998 | Ockuly et al. |
| 5,724,975 A | 3/1998 | Negus et al. |
| 5,725,512 A | 3/1998 | Swartz et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,880 A | 5/1998 | Banas et al. |
| 5,749,883 A | 5/1998 | Halpern |
| 5,749,894 A | 5/1998 | Engelson |
| 5,766,219 A | 6/1998 | Horton |
| 5,766,246 A | 6/1998 | Mulhauser et al. |
| 5,769,816 A | 6/1998 | Barbut et al. |
| 5,776,097 A | 7/1998 | Massoud |
| 5,776,162 A | 7/1998 | Kleshinski |
| 5,782,860 A | 7/1998 | Epstein et al. |
| 5,785,679 A | 7/1998 | Abolfathi et al. |
| 5,800,454 A | 9/1998 | Jacobsen et al. |
| 5,800,457 A | 9/1998 | Gelbfish |
| 5,800,512 A | 9/1998 | Letnz et al. |
| 5,807,261 A | 9/1998 | Benaron et al. |
| 5,810,874 A | 9/1998 | Lefebvre |
| 5,814,028 A | 9/1998 | Swartz et al. |
| 5,814,029 A | 9/1998 | Hassett |
| 5,814,064 A | 9/1998 | Daniel |
| 5,820,591 A | 10/1998 | Thompson et al. |

(56) References Cited

U.S. PATENT DOCUMENTS

| | | |
|---|---|---|
| 5,823,198 A | 10/1998 | Jones et al. |
| 5,830,228 A | 11/1998 | Knapp et al. |
| 5,833,673 A | 11/1998 | Ockuly et al. |
| 5,836,913 A | 11/1998 | Orth et al. |
| 5,836,968 A | 11/1998 | Simon et al. |
| 5,840,027 A | 11/1998 | Swartz et al. |
| 5,843,118 A | 12/1998 | Sepetka et al. |
| 5,846,260 A | 12/1998 | Maahs |
| 5,846,261 A | 12/1998 | Kotula et al. |
| 5,848,969 A | 12/1998 | Panescu et al. |
| 5,849,005 A | 12/1998 | Garrison et al. |
| 5,851,232 A | 12/1998 | Lois |
| 5,853,422 A | 12/1998 | Huebsch et al. |
| 5,855,597 A | 1/1999 | Jayaraman |
| 5,865,791 A | 2/1999 | Whayne et al. |
| 5,865,802 A | 2/1999 | Yoon et al. |
| 5,868,702 A | 2/1999 | Stevens et al. |
| 5,868,708 A | 2/1999 | Hart et al. |
| 5,876,367 A | 3/1999 | Kaganov et al. |
| 5,879,296 A | 3/1999 | Ockuly et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,902,289 A | 5/1999 | Swartz et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,925,060 A | 7/1999 | Forber |
| 5,925,063 A | 7/1999 | Khosravi |
| 5,925,074 A | 7/1999 | Gingras et al. |
| 5,925,075 A | 7/1999 | Myers et al. |
| 5,928,192 A | 7/1999 | Maahs |
| 5,928,260 A | 7/1999 | Chin et al. |
| 5,931,818 A | 8/1999 | Werp et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,941,896 A | 8/1999 | Kerr |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,954,767 A | 9/1999 | Pajotin et al. |
| 5,957,940 A | 9/1999 | Tanner et al. |
| 5,961,545 A | 10/1999 | Lentz et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,280 A | 12/1999 | Buck et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,013,093 A | 1/2000 | Nott et al. |
| 6,024,751 A | 2/2000 | Lovato et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,036,720 A | 3/2000 | Abrams et al. |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,063,113 A | 5/2000 | Kavteladze et al. |
| 6,066,126 A | 5/2000 | Li et al. |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,090,084 A | 7/2000 | Hassett et al. |
| 6,096,052 A | 8/2000 | Callister et al. |
| 6,096,053 A | 8/2000 | Bates et al. |
| 6,110,243 A | 8/2000 | Wnenchak et al. |
| 6,123,715 A | 9/2000 | Amplatz |
| 6,124,523 A | 9/2000 | Banas et al. |
| 6,132,438 A | 10/2000 | Fleischman et al. |
| 6,135,991 A | 10/2000 | Muni et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,152,946 A | 11/2000 | Broome et al. |
| 6,156,055 A | 12/2000 | Ravenscroft |
| 6,159,195 A | 12/2000 | Ha et al. |
| 6,161,543 A | 12/2000 | Cox et al. |
| 6,168,615 B1 | 1/2001 | Ken et al. |
| 6,171,329 B1 | 1/2001 | Shaw et al. |
| 6,179,859 B1 | 1/2001 | Bates et al. |
| 6,193,739 B1 | 2/2001 | Chevillon et al. |
| 6,203,531 B1 | 3/2001 | Ockuly et al. |
| 6,206,907 B1 | 3/2001 | Marino et al. |
| 6,214,029 B1 | 4/2001 | Thill et al. |
| 6,221,092 B1 | 4/2001 | Koike et al. |
| 6,231,561 B1 | 5/2001 | Frazier et al. |
| 6,231,589 B1 | 5/2001 | Wessman et al. |
| 6,235,045 B1 | 5/2001 | Barbut et al. |
| 6,245,012 B1 | 6/2001 | Kleshinski |
| 6,251,122 B1 | 6/2001 | Tsukernik |
| 6,258,115 B1 | 7/2001 | Dubrul |
| 6,267,772 B1 | 7/2001 | Mulhauser et al. |
| 6,267,776 B1 | 7/2001 | O'Connell |
| 6,270,490 B1 | 8/2001 | Hahnen |
| 6,270,530 B1 | 8/2001 | Eldridge et al. |
| 6,270,902 B1 | 8/2001 | Tedeschi et al. |
| 6,277,138 B1 | 8/2001 | Levinson et al. |
| 6,285,898 B1 | 9/2001 | Ben-Haim |
| 6,290,674 B1 | 9/2001 | Roue et al. |
| 6,290,708 B1 | 9/2001 | Kugel et al. |
| 6,312,407 B1 | 11/2001 | Zadno-Azizi et al. |
| 6,319,251 B1 | 11/2001 | Tu et al. |
| 6,328,727 B1 | 12/2001 | Frazier et al. |
| 6,328,755 B1 | 12/2001 | Marshall |
| 6,342,062 B1 | 1/2002 | Suon et al. |
| 6,346,116 B1 | 2/2002 | Brooks et al. |
| 6,346,895 B1 | 2/2002 | Lee et al. |
| 6,361,545 B1 | 3/2002 | Macoviak et al. |
| 6,364,895 B1 | 4/2002 | Greenhalgh |
| 6,368,338 B1 | 4/2002 | Kónya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,398,803 B1 | 6/2002 | Layne et al. |
| 6,402,746 B1 | 6/2002 | Whayne et al. |
| 6,402,771 B1 | 6/2002 | Palmer et al. |
| 6,402,779 B1 | 6/2002 | Colone et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,454,775 B1 | 9/2002 | Demarais et al. |
| 6,458,145 B1 | 10/2002 | Ravenscroft et al. |
| 6,464,712 B1 | 10/2002 | Epstein et al. |
| 6,468,291 B2 | 10/2002 | Bates et al. |
| 6,468,301 B1 | 10/2002 | Amplatz et al. |
| 6,485,501 B1 | 11/2002 | Green |

(56) References Cited

U.S. PATENT DOCUMENTS

| | | |
|---|---|---|
| 6,488,689 B1 | 12/2002 | Kaplan et al. |
| 6,511,496 B1 | 1/2003 | Huter et al. |
| 6,514,280 B1 | 2/2003 | Gilson |
| 6,517,573 B1 | 2/2003 | Pollock et al. |
| 6,533,782 B2 | 3/2003 | Howell et al. |
| 6,547,760 B1 | 4/2003 | Samson et al. |
| 6,547,815 B2 | 4/2003 | Myers |
| 6,551,303 B1 | 4/2003 | Van Tassel et al. |
| 6,551,344 B2 | 4/2003 | Thill |
| 6,558,401 B1 | 5/2003 | Azizi |
| 6,558,405 B1 | 5/2003 | McInnes |
| 6,558,414 B2 | 5/2003 | Layne |
| 6,562,058 B2 | 5/2003 | Seguin et al. |
| 6,569,184 B2 | 5/2003 | Huter |
| 6,569,214 B2 | 5/2003 | Williams et al. |
| 6,589,214 B2 | 7/2003 | McGuckin et al. |
| 6,589,251 B2 | 7/2003 | Yee et al. |
| 6,599,308 B2 | 7/2003 | Amplatz |
| 6,602,271 B2 | 8/2003 | Adams et al. |
| 6,623,508 B2 | 9/2003 | Shaw et al. |
| 6,641,564 B1 | 11/2003 | Kraus |
| 6,650,923 B1 | 11/2003 | Lesh et al. |
| 6,652,555 B1 | 11/2003 | VanTassel et al. |
| 6,652,556 B1 | 11/2003 | VanTassel et al. |
| 6,666,861 B1 | 12/2003 | Grabek |
| 6,689,150 B1 | 2/2004 | Vantassel et al. |
| 6,699,260 B2 | 3/2004 | Dubrul et al. |
| 6,699,276 B2 | 3/2004 | Sogard et al. |
| 6,702,825 B2 | 3/2004 | Frazier et al. |
| 6,712,836 B1 | 3/2004 | Berg et al. |
| 6,726,701 B2 | 4/2004 | Gilson et al. |
| 6,730,108 B2 | 5/2004 | Van Tassel et al. |
| 6,755,812 B2 | 6/2004 | Peterson et al. |
| 6,827,737 B2 | 12/2004 | Hill et al. |
| 6,837,901 B2 | 1/2005 | Rabkin et al. |
| 6,855,153 B2 | 2/2005 | Saadat |
| 6,911,037 B2 | 6/2005 | Gainor et al. |
| 6,932,838 B2 | 8/2005 | Schwartz et al. |
| 6,942,653 B2 | 9/2005 | Quinn |
| 6,949,113 B2 | 9/2005 | Van Tassel et al. |
| 6,958,061 B2 | 10/2005 | Truckai et al. |
| 6,994,092 B2 | 2/2006 | van der Burg et al. |
| 7,011,671 B2 | 3/2006 | Welch |
| 7,014,645 B2 | 3/2006 | Greene, Jr. et al. |
| 7,037,321 B2 | 5/2006 | Sachdeva et al. |
| 7,044,134 B2 | 5/2006 | Khairkhahan et al. |
| 7,097,651 B2 | 8/2006 | Harrison et al. |
| 7,128,073 B1 | 10/2006 | van der Burg et al. |
| 7,152,605 B2 | 12/2006 | Khairkhahan et al. |
| 7,169,164 B2 | 1/2007 | Borillo et al. |
| 7,179,275 B2 | 2/2007 | McGuckin, Jr. et al. |
| 7,226,466 B2 | 6/2007 | Opolski |
| 7,303,526 B2 | 12/2007 | Sharkey et al. |
| 7,323,002 B2 | 1/2008 | Johnson et al. |
| 7,597,704 B2 | 10/2009 | Frazier et al. |
| 7,678,123 B2 | 3/2010 | Chanduszko |
| 7,695,425 B2 | 4/2010 | Schweich et al. |
| 7,713,282 B2 | 5/2010 | Frazier et al. |
| 7,722,641 B2 | 5/2010 | van der Burg et al. |
| 7,727,189 B2 | 6/2010 | VanTassel et al. |
| 7,735,493 B2 | 6/2010 | van der Burg et al. |
| 7,780,694 B2 | 8/2010 | Palmer et al. |
| 7,799,049 B2 | 9/2010 | Ostrovsky et al. |
| 7,811,300 B2 | 10/2010 | Feller, III et al. |
| 7,811,314 B2 | 10/2010 | Fierens et al. |
| 7,862,500 B2 | 1/2011 | Khairkhahan et al. |
| 7,927,365 B2 | 4/2011 | Fierens et al. |
| 7,972,359 B2 | 7/2011 | Kreidler |
| 8,025,495 B2 | 9/2011 | Hardert et al. |
| 8,043,329 B2 | 10/2011 | Khairkhahan et al. |
| 8,052,715 B2 | 11/2011 | Quinn et al. |
| 8,062,282 B2 | 11/2011 | Kolb |
| 8,080,032 B2 | 12/2011 | van der Burg et al. |
| 8,097,015 B2 | 1/2012 | Devellian |
| 8,221,384 B2 | 7/2012 | Frazier et al. |
| 8,221,445 B2 | 7/2012 | van Tassel et al. |
| 8,287,563 B2 | 10/2012 | Khairkhahan et al. |
| 8,323,309 B2 | 12/2012 | Khairkhahan et al. |
| 8,388,672 B2 | 3/2013 | Khairkhahan et al. |
| 8,491,623 B2 | 7/2013 | Vogel et al. |
| 8,523,897 B2 | 9/2013 | van der Burg et al. |
| 8,535,343 B2 | 9/2013 | van der Burg et al. |
| 8,562,509 B2 | 10/2013 | Bates |
| 8,663,273 B2 | 3/2014 | Khairkhahan et al. |
| 8,685,055 B2 | 4/2014 | VanTassel et al. |
| 8,834,519 B2 | 9/2014 | van der Burg et al. |
| 8,845,711 B2 | 9/2014 | Miles et al. |
| 9,034,006 B2 | 5/2015 | Quinn et al. |
| 9,132,000 B2 | 9/2015 | VanTassel et al. |
| 9,168,043 B2 | 10/2015 | van der Burg et al. |
| 9,211,124 B2 | 12/2015 | Campbell et al. |
| 9,445,895 B2 | 9/2016 | Kreidler |
| 9,554,806 B2 | 1/2017 | Larsen et al. |
| 9,561,037 B2 | 2/2017 | Fogarty et al. |
| 9,561,097 B1 | 2/2017 | Kim et al. |
| 9,629,636 B2 | 4/2017 | Fogarty et al. |
| 9,730,701 B2 | 8/2017 | Tischler et al. |
| 9,883,936 B2 | 2/2018 | Sutton et al. |
| 9,913,652 B2 | 3/2018 | Bridgeman et al. |
| 9,943,299 B2 | 4/2018 | Khairkhahan et al. |
| 9,943,315 B2 | 4/2018 | Kaplan et al. |
| 10,071,181 B1 | 9/2018 | Penegor et al. |
| 10,076,335 B2 | 9/2018 | Zaver et al. |
| 10,143,458 B2 | 12/2018 | Kreidler |
| 2001/0000797 A1 | 5/2001 | Mazzocchi |
| 2001/0020181 A1 | 9/2001 | Layne |
| 2001/0034537 A1 | 10/2001 | Shaw et al. |
| 2001/0037141 A1 | 11/2001 | Yee et al. |
| 2002/0022860 A1 | 2/2002 | Borillo et al. |
| 2002/0035374 A1 | 3/2002 | Borillo et al. |
| 2002/0045931 A1 | 4/2002 | Sogard et al. |
| 2002/0062133 A1 | 5/2002 | Gilson et al. |
| 2002/0082638 A1 | 6/2002 | Porter et al. |
| 2002/0082675 A1 | 6/2002 | Myers |
| 2002/0099439 A1 | 7/2002 | Schwartz et al. |
| 2002/0111647 A1 | 8/2002 | Khairkhahan et al. |
| 2002/0138094 A1 | 9/2002 | Borillo et al. |
| 2002/0138097 A1 | 9/2002 | Ostrovsky et al. |
| 2002/0169475 A1 | 11/2002 | Gainor et al. |
| 2002/0177855 A1 | 11/2002 | Greene, Jr. et al. |
| 2003/0017775 A1 | 1/2003 | Dong et al. |
| 2003/0023262 A1 | 1/2003 | Welch |
| 2003/0023266 A1 | 1/2003 | Borillo et al. |
| 2003/0057156 A1 | 3/2003 | Peterson et al. |
| 2003/0060871 A1 | 3/2003 | Hill et al. |
| 2003/0120337 A1 | 6/2003 | Van Tassel et al. |
| 2003/0125601 A1* | 7/2003 | Schock ............ A61B 5/0215 600/18 |
| 2003/0181942 A1 | 9/2003 | Sutton et al. |
| 2003/0191526 A1 | 10/2003 | Van Tassel et al. |
| 2003/0195555 A1 | 10/2003 | Khairkhahan et al. |
| 2003/0204203 A1 | 10/2003 | Khairkhahan et al. |
| 2003/0208214 A1 | 11/2003 | Loshakove et al. |
| 2003/0220667 A1 | 11/2003 | van der Burg et al. |
| 2004/0034366 A1 | 2/2004 | van der Burg et al. |
| 2004/0049210 A1 | 3/2004 | VanTassel et al. |
| 2004/0093012 A1 | 5/2004 | Cully et al. |
| 2004/0098031 A1 | 5/2004 | van der Burg et al. |
| 2004/0122467 A1 | 6/2004 | VanTassel et al. |
| 2004/0127935 A1 | 7/2004 | VanTassel et al. |
| 2004/0158274 A1 | 8/2004 | WasDyke |
| 2004/0186486 A1 | 9/2004 | Roue et al. |
| 2004/0215230 A1 | 10/2004 | Frazier et al. |
| 2004/0220610 A1 | 11/2004 | Kreidler et al. |
| 2004/0220682 A1 | 11/2004 | Levine et al. |
| 2004/0230222 A1 | 11/2004 | van der Burg et al. |
| 2005/0004652 A1 | 1/2005 | van der Burg et al. |
| 2005/0015109 A1 | 1/2005 | Lichtenstein |
| 2005/0038470 A1 | 2/2005 | van der Burg et al. |
| 2005/0049573 A1 | 3/2005 | Van Tassel et al. |
| 2005/0070952 A1 | 3/2005 | Devellian |
| 2005/0113861 A1 | 5/2005 | Corcoran et al. |
| 2005/0125020 A1 | 6/2005 | Meade et al. |
| 2005/0177182 A1 | 8/2005 | van der Burg et al. |

(56) References Cited

U.S. PATENT DOCUMENTS

| | | |
|---|---|---|
| 2005/0203568 A1 | 9/2005 | Burg et al. |
| 2005/0283186 A1 | 12/2005 | Berrada et al. |
| 2005/0288704 A1 | 12/2005 | Cartier et al. |
| 2006/0015136 A1 | 1/2006 | Besselink |
| 2006/0030877 A1 | 2/2006 | Martinez et al. |
| 2006/0052816 A1 | 3/2006 | Bates et al. |
| 2006/0100658 A1 | 5/2006 | Obana et al. |
| 2006/0155323 A1 | 7/2006 | Porter et al. |
| 2007/0066913 A1* | 3/2007 | Patangay ............ A61B 5/02028 600/528 |
| 2007/0066993 A1 | 3/2007 | Kreidler |
| 2007/0083227 A1 | 4/2007 | van der Burg et al. |
| 2007/0083230 A1 | 4/2007 | Javois |
| 2007/0088223 A1* | 4/2007 | Mann .................... A61B 5/349 600/485 |
| 2007/0129637 A1* | 6/2007 | Wolinsky ............ A61B 5/02152 600/549 |
| 2007/0150041 A1 | 6/2007 | Evans et al. |
| 2007/0156123 A1 | 7/2007 | Moll et al. |
| 2007/0162048 A1 | 7/2007 | Quinn et al. |
| 2007/0185471 A1 | 8/2007 | Johnson |
| 2008/0004536 A1* | 1/2008 | Baxi .................... A61B 5/304 600/509 |
| 2008/0275536 A1 | 11/2008 | Zarins et al. |
| 2009/0005803 A1 | 1/2009 | Batiste |
| 2009/0062841 A1 | 3/2009 | Amplatz et al. |
| 2009/0099647 A1 | 4/2009 | Glimsdale et al. |
| 2009/0105747 A1 | 4/2009 | Chanduszko et al. |
| 2009/0112249 A1 | 4/2009 | Miles et al. |
| 2009/0254195 A1 | 10/2009 | Khairkhan et al. |
| 2009/0318948 A1 | 12/2009 | Linder et al. |
| 2010/0004726 A1 | 1/2010 | Hancock et al. |
| 2010/0049238 A1 | 2/2010 | Simpson |
| 2010/0106178 A1 | 4/2010 | Obermiller et al. |
| 2010/0324585 A1 | 12/2010 | Miles et al. |
| 2011/0054515 A1 | 3/2011 | Bridgeman et al. |
| 2011/0082495 A1 | 4/2011 | Ruiz |
| 2011/0098525 A1 | 4/2011 | Kermode et al. |
| 2011/0218566 A1 | 9/2011 | van der Burg et al. |
| 2011/0301630 A1 | 12/2011 | Hendriksen et al. |
| 2012/0029553 A1 | 2/2012 | Quinn et al. |
| 2012/0035643 A1 | 2/2012 | Khairkhahan et al. |
| 2012/0065662 A1 | 3/2012 | van der Burg et al. |
| 2012/0125619 A1 | 5/2012 | Wood et al. |
| 2012/0172654 A1 | 7/2012 | Bates |
| 2012/0172927 A1 | 7/2012 | Campbell et al. |
| 2012/0239077 A1 | 9/2012 | Zaver et al. |
| 2012/0239083 A1 | 9/2012 | Kreidler |
| 2012/0245619 A1 | 9/2012 | Guest |
| 2012/0283585 A1 | 11/2012 | Werneth et al. |
| 2012/0283773 A1 | 11/2012 | Van Tassel et al. |
| 2012/0323267 A1 | 12/2012 | Ren |
| 2013/0006343 A1 | 1/2013 | Kassab et al. |
| 2013/0012982 A1 | 1/2013 | Khairkhahan et al. |
| 2013/0018413 A1 | 1/2013 | Oral et al. |
| 2013/0110154 A1 | 5/2013 | van der Burg et al. |
| 2013/0165735 A1 | 6/2013 | Khairkhahan et al. |
| 2013/0211492 A1 | 8/2013 | Schneider et al. |
| 2013/0331884 A1 | 12/2013 | Van der Burg et al. |
| 2014/0018841 A1 | 1/2014 | Peiffer et al. |
| 2014/0039536 A1 | 2/2014 | Cully et al. |
| 2014/0046360 A1 | 2/2014 | van der Burg et al. |
| 2014/0081314 A1 | 3/2014 | Zaver et al. |
| 2014/0100596 A1 | 4/2014 | Rudman et al. |
| 2014/0142612 A1 | 5/2014 | Li et al. |
| 2014/0148842 A1 | 5/2014 | Khairkhahan et al. |
| 2014/0163605 A1 | 6/2014 | VanTassel et al. |
| 2014/0188157 A1 | 7/2014 | Clark |
| 2014/0303719 A1 | 10/2014 | Cox et al. |
| 2014/0336612 A1 | 11/2014 | Frydlewski et al. |
| 2014/0336699 A1 | 11/2014 | van der Burg et al. |
| 2015/0005810 A1 | 1/2015 | Center et al. |
| 2015/0039021 A1 | 2/2015 | Khairkhahan et al. |
| 2015/0080903 A1 | 3/2015 | Dillard et al. |
| 2015/0196300 A1 | 7/2015 | Tischler et al. |
| 2015/0230909 A1 | 8/2015 | Zaver et al. |
| 2015/0238197 A1 | 8/2015 | Quinn et al. |
| 2015/0305727 A1 | 10/2015 | Karimov et al. |
| 2015/0313604 A1 | 11/2015 | Roue et al. |
| 2015/0313605 A1 | 11/2015 | Griffin |
| 2015/0327979 A1 | 11/2015 | Quinn et al. |
| 2015/0374491 A1 | 12/2015 | Kreidler |
| 2016/0051358 A1 | 2/2016 | Sutton et al. |
| 2016/0058539 A1 | 3/2016 | VanTassel et al. |
| 2016/0066922 A1 | 3/2016 | Bridgeman et al. |
| 2016/0106437 A1 | 4/2016 | van der Burg et al. |
| 2016/0192942 A1 | 7/2016 | Strauss et al. |
| 2016/0287259 A1 | 10/2016 | Hanson et al. |
| 2016/0331382 A1 | 11/2016 | Center et al. |
| 2016/0374657 A1 | 12/2016 | Kreidler |
| 2017/0027552 A1 | 2/2017 | Turkington et al. |
| 2017/0042550 A1 | 2/2017 | Chakraborty et al. |
| 2017/0056166 A1 | 3/2017 | Ratz et al. |
| 2017/0100112 A1 | 4/2017 | van der Burg et al. |
| 2017/0181751 A1 | 6/2017 | Larsen et al. |
| 2017/0340336 A1 | 11/2017 | Osypka |
| 2018/0064446 A1 | 3/2018 | Figulla et al. |
| 2018/0070950 A1 | 3/2018 | Zaver et al. |
| 2018/0140412 A1 | 5/2018 | Sutton et al. |
| 2018/0140413 A1 | 5/2018 | Quinn et al. |
| 2018/0250014 A1 | 9/2018 | Melanson et al. |
| 2019/0223883 A1 | 7/2019 | Anderson et al. |
| 2020/0205840 A1* | 7/2020 | Adawi .............. A61B 17/12177 |

FOREIGN PATENT DOCUMENTS

| | | |
|---|---|---|
| CN | 106859722 A | 6/2017 |
| DE | 10201004476 A1 | 3/2012 |
| EP | 1523957 A2 | 4/2005 |
| EP | 1595504 A1 | 11/2005 |
| EP | 2074953 A1 | 1/2009 |
| EP | 2481381 A1 | 8/2012 |
| EP | 2928420 A1 | 10/2015 |
| EP | 3072461 A1 | 9/2016 |
| EP | 3372173 A2 | 9/2018 |
| JP | 2003532457 A | 11/2003 |
| JP | 2005324019 A | 11/2005 |
| JP | 2007513684 A | 5/2007 |
| JP | 2009160402 A | 7/2009 |
| JP | 2012501793 A | 1/2012 |
| WO | 9313712 A1 | 7/1993 |
| WO | 9504132 A1 | 2/1995 |
| WO | 9522359 A1 | 8/1995 |
| WO | 9601591 A1 | 1/1996 |
| WO | 9640356 A1 | 12/1996 |
| WO | 9721402 A1 | 6/1997 |
| WO | 9726939 A1 | 7/1997 |
| WO | 9728749 A1 | 8/1997 |
| WO | 9735522 A1 | 10/1997 |
| WO | 9802100 A1 | 1/1998 |
| WO | 9817187 A1 | 4/1998 |
| WO | 9822026 A1 | 5/1998 |
| WO | 9823322 A1 | 6/1998 |
| WO | 9827868 A1 | 7/1998 |
| WO | 9905977 A1 | 2/1999 |
| WO | 9907289 A1 | 2/1999 |
| WO | 9908607 A1 | 2/1999 |
| WO | 9923976 A1 | 5/1999 |
| WO | 9925252 A1 | 5/1999 |
| WO | 9930640 A1 | 6/1999 |
| WO | 9944510 A1 | 9/1999 |
| WO | 9959479 A1 | 11/1999 |
| WO | 0001308 A1 | 1/2000 |
| WO | 0016705 A1 | 3/2000 |
| WO | 0027292 A1 | 5/2000 |
| WO | 0035352 A1 | 6/2000 |
| WO | 0053120 A1 | 9/2000 |
| WO | 0067669 A1 | 11/2000 |
| WO | 0108743 A1 | 2/2001 |
| WO | 0115629 A1 | 3/2001 |
| WO | 0121247 A1 | 3/2001 |
| WO | 0126726 A1 | 4/2001 |
| WO | 0130266 A1 | 5/2001 |
| WO | 0130267 A1 | 5/2001 |

(56) References Cited

FOREIGN PATENT DOCUMENTS

| WO | 0130268 A1 | 5/2001 |
| WO | 0170119 A1 | 9/2001 |
| WO | 0215793 A2 | 2/2002 |
| WO | 0224106 A2 | 3/2002 |
| WO | 02071977 A2 | 9/2002 |
| WO | 03007825 A1 | 1/2003 |
| WO | 03008030 A2 | 1/2003 |
| WO | 03032818 A1 | 4/2003 |
| WO | 2004012629 A1 | 2/2004 |
| WO | 2007044536 A1 | 4/2007 |
| WO | 2010024801 A1 | 3/2010 |
| WO | 2010081033 A1 | 7/2010 |
| WO | 2013060855 A1 | 5/2013 |
| WO | 2013159065 A1 | 10/2013 |
| WO | 2014011865 A1 | 1/2014 |
| WO | 2014018907 A1 | 1/2014 |
| WO | 2014089129 A1 | 6/2014 |
| WO | 201406239 A1 | 7/2014 |
| WO | 2015164836 A1 | 10/2015 |
| WO | 2016087145 A1 | 6/2016 |
| WO | 2018017935 A1 | 1/2018 |
| WO | 2018187732 A1 | 10/2018 |
| WO | 2019084358 A1 | 5/2019 |
| WO | WO-2019136218 A1 * | 7/2019 ........... A61B 5/0006 |

OTHER PUBLICATIONS

International Search Report and Written Opinion dated Feb. 15, 2000 for International Application No. PCT/US99/26325.

International Search Report dated May 20, 2003 for International Application No. PCT/US02/33808.

Written Opinion dated Nov. 17, 2003 for International Application No. PCT/US/02/33808.

International Search Report and Written Opinion dated Aug. 21, 2018 for International Application No. PCT/US2018/029684.

Cragg et al., "A New Percutaneous Vena Cava Filter," American Journal of Radiology, Sep. 1983, pp. 601-604, vol. 141.

Cragg et al., "Nonsurgical Placement of Arterial Endoprostheses: A New Technique Using Nitinol Wire," Radiology, Apr. 1983, pp. 261-263, vol. 147, No. 1.

Lock et al., "Transcatheter Closure of Atrial Septal Defects." Circulation, May 1989, pp. 1091-1099, vol. 79, No. 5.

Lock et al., "Transcatheter Umbrella Closure of Congenital Heart Defects," Circulation, Mar. 1987, pp. 593-599, vol. 75, No. 3.

Rashkind et al., "Nonsurgical closure of patent ductus arteriosus: clinical application of the Rashkind PDA Occluder System," Circulation, Mar. 1987, pp. 583-592, vol. 75, No. 3.

Rosengart et al., "Percutaneous and Minimally Invasive Valve Procedures," Circulation, Apr. 1, 2008, pp. 1750-1767, vol. 117.

Ruttenberg, "Nonsurgical Therapy of Cardiac Disorders," Pediatric Consult, 1986, Pages not numbered, vol. 5, No. 2.

Sugita et al., "Nonsurgical Implantations of a Vascular Ring Prosthesis Using Thermal Shape Memory Ti/Ni Alloy (Nitinol Wire)," Trans. Am. Soc. Artif. Intern. Organs, 1986, pp. 30-34, vol. XXXII.

Wessel et al., "Outpatient Closure of the Patent Ductus Arteriousus," Circulation, 1988, pp. 1068-1071, vol. 77, No. 5.

Tung et al., U.S. Appl. No. 61/559,941, filed Nov. 15, 2011.

Yue Yu et al., U.S. Appl. No. 61/557,880, filed Dec. 20, 2011.

Cline, "File: Fish hooks.jpg," Wikipedia foundation , Inc., San Francisco, CA, Jun. 2007; p. 1 of 4; available online at http://en.wikipedia.org/wiki/File:Fish_hooks.jpg; last accessed Oct. 5, 2012.

International Search Report and Written Opinion dated Apr. 22, 2014 for International Application No. PCT/US2013/078454.

Aryana et al., "Incomplete Closure of the Left Atrial Appendage: Implication and Management." Curr Cardiol Rep., 18(9):82, 2016.

Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.

University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019.

Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.

Romero et al., "Left Atrial Appendage Closure Devices," Clinical Medicine Insights: Cardiology, vol. 8, pp. 45-52, 2014.

Invitation to Pay Additional Fees and, Where Applicable, Protest Fee, mailed Oct. 13, 2016.

International Search Report and Written Opinion dated Oct. 14, 2019 for International Application No. PCT/US2019/047452.

International Search Report and Written Opinion dated Oct. 27, 2017 for International Application No. PCT/US2017/048150.

International Search Report and Written Opinion dated Jan. 21, 2019 for International Application No. PCT/US2018/051953.

International Search Report and Written Opinion dated Oct. 13, 2016 for International Application No. PCT/US2016/043363.

International Search Report and Written Opinion dated Mar. 17, 2020, for International Application No. PCT/US2019/065243.

International Search Report and Written Opinion dated Sep. 9, 2019 for International Application No. PCT/US2019/033698.

Blackshear et al; "Appendage Obliteration to Reduce Stroke in Cardiac Surgical Patients with Atrial Fibrillation", Ann. Thoracic Surgery, pp. 755-759, 1996.

Lindsay, "Obliteration of the Left Atrial Appendage: A Concept Worth Testing", Ann. Thoracic Surgery, 1996.

Invitation to Pay Additional Fees dated Feb. 22, 2019 for International Application No. PCT/US2018/066163.

International Search Report and Written Opinion dated Oct. 23, 2020 for International Application No. PCT/US2020/042192.

Rudnitskaya, "Calibration Update and Drift Correction for Electronic Noses and Tongues," Frontiers of Chemistry, vol. 6, Article 433, 17 Pages, Sep. 25, 2018.

* cited by examiner

MEDICAL SYSTEM FOR TREATING A LEFT ATRIAL APPENDAGE

CROSS-REFERENCE TO RELATED APPLICATIONS

This application claims the benefit of priority of U.S. Provisional Application No. 63/145,144 filed Feb. 3, 2021, the entire disclosure of which is hereby incorporated by reference.

TECHNICAL FIELD

The disclosure relates generally to medical devices and more particularly to medical devices that are adapted for use in percutaneous medical procedures including implantation into the left atrial appendage (LAA) of a heart.

BACKGROUND

The left atrial appendage is a small organ attached to the left atrium of the heart. During normal heart function, as the left atrium constricts and forces blood into the left ventricle, the left atrial appendage constricts and forces blood into the left atrium. The ability of the left atrial appendage to contract assists with improved filling of the left ventricle, thereby playing a role in maintaining cardiac output. However, in patients suffering from atrial fibrillation, the left atrial appendage may not properly contract or empty, causing stagnant blood to pool within its interior, which can lead to the undesirable formation of thrombi within the left atrial appendage.

Thrombi forming in the left atrial appendage may break loose from this area and enter the blood stream. Emboli that migrate through the blood vessels may eventually plug a smaller vessel downstream and thereby contribute to stroke or heart attack. Clinical studies have shown that the majority of blood clots in patients with atrial fibrillation originate in the left atrial appendage. As a treatment, medical devices have been developed which are deployed to close off the left atrial appendage. Of the known medical devices and methods, each has certain advantages and disadvantages. There is an ongoing need to provide alternative medical devices and introducers as well as alternative methods for manufacturing and using medical devices and introducers.

SUMMARY

In one example, a medical system for monitoring a left atrial pressure in a heart of a patient may comprise: an implantable device including an expandable framework and a first sensor secured to the expandable framework; and an external component configured to communicate wirelessly with the implantable device. The first sensor may be configured to detect a first measurement. The first sensor may be a pressure sensor and the first measurement may be the left atrial pressure. The implantable device or the external component may include a processor configured to create a first trend for the first measurement. The processor may be configured to use the first trend to modify the first measurement prior to outputting a corrected result.

In addition or alternatively to any example described herein, the processor is configured to use the first trend to remove drift from the first measurement prior to outputting the corrected result.

In addition or alternatively to any example described herein, the medical system may further comprise a second sensor secured to the expandable framework. The second sensor may be configured to detect a second measurement that is a surrogate for the left atrial pressure.

In addition or alternatively to any example described herein, the processor is configured to create a second trend for the second measurement.

In addition or alternatively to any example described herein, the processor is configured to use the first trend and the second trend to modify the first measurement prior to outputting the corrected result.

In addition or alternatively to any example described herein, the processor uses the second trend to correct the first measurement for drift.

In addition or alternatively to any example described herein, the second measurement is a third heart sound (S3).

In addition or alternatively to any example described herein, the second sensor has a different sensing modality than the first sensor.

In addition or alternatively to any example described herein, the second sensor is an accelerometer.

In addition or alternatively to any example described herein, the second sensor is an acoustic sensor.

In addition or alternatively to any example described herein, the medical system may further comprise a second sensor disposed in a second medical device configured to be in contact with a body of the patient. The second sensor may be configured to detect a second measurement that is a surrogate for the left atrial pressure when the second medical device is in contact with the body of the patient and send the second measurement to the external component.

In addition or alternatively to any example described herein, a method of autonomous recalibration of a pressure sensor used to detect a left atrial pressure within a heart of a patient may comprise:
  detecting signals of the left atrial pressure using a first sensor coupled to an expandable framework, the expandable framework being implantable within a left atrial appendage of the heart of the patient;
  detecting signals of a third heart sound (S3) from the heart of the patient using a second sensor coupled to the expandable framework;
  using the signals of the left atrial pressure to establish a trend of the left atrial pressure with a processor;
  using the signals of the third heart sound to establish a trend of the third heart sound with the processor;
  comparing the trend of the left atrial pressure to the trend of the third heart sound with the processor to determine if the first sensor is experiencing drift; and
  using the trend of the third heart sound to correct the trend of the left atrial pressure to remove the drift with the processor;
  outputting a corrected trend of the left atrial pressure devoid of the drift.

In addition or alternatively to any example described herein, comparing the trend of the left atrial pressure to the trend of the third heart sound includes comparing a slope of the trend of the left atrial pressure to a slope of the trend of the third heart sound.

In addition or alternatively to any example described herein, using the trend of the third heart sound to correct the trend of the left atrial pressure to remove the drift includes subtracting a difference between the slope of the trend of the third heart sound and the slope of the trend of the left atrial pressure from the trend of the left atrial pressure.

In addition or alternatively to any example described herein, when the drift exceeds a predetermined limit, the method further includes issuing a warning to manually recalibrate the first sensor.

In addition or alternatively to any example described herein, the first sensor has a first sensing modality and responds to a first set of daily physiological changes, and the second sensor has a second sensing modality different from the first sensing modality and responds to the first set of daily physiological changes.

In addition or alternatively to any example described herein, a medical system for monitoring a left atrial pressure in a heart of a patient may comprise: an implantable device including an expandable framework and a first sensor secured to the expandable framework; and an external component configured to communicate wirelessly with the implantable device. The first sensor may be configured to detect a first measurement. The first sensor may be a pressure sensor and the first measurement may be the left atrial pressure. The system may further include a processor and a signal filter. The signal filter may be used by the processor to modify the first measurement prior to outputting a corrected result.

In addition or alternatively to any example described herein, the signal filter is a low pass filter configured to create a signal representative of drift in the first measurement.

In addition or alternatively to any example described herein, the processor subtracts the signal representative of drift from the first measurement to produce the corrected result.

In addition or alternatively to any example described herein, the low pass filter has a frequency cutoff at about $10^{-7}$ Hertz.

In addition or alternatively to any example described herein, the signal filter is a high pass filter configured to remove a portion of the first measurement corresponding to drift in the first sensor to produce the corrected result.

In addition or alternatively to any example described herein, the high pass filter has a frequency cutoff at about $10^{-7}$ Hertz.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
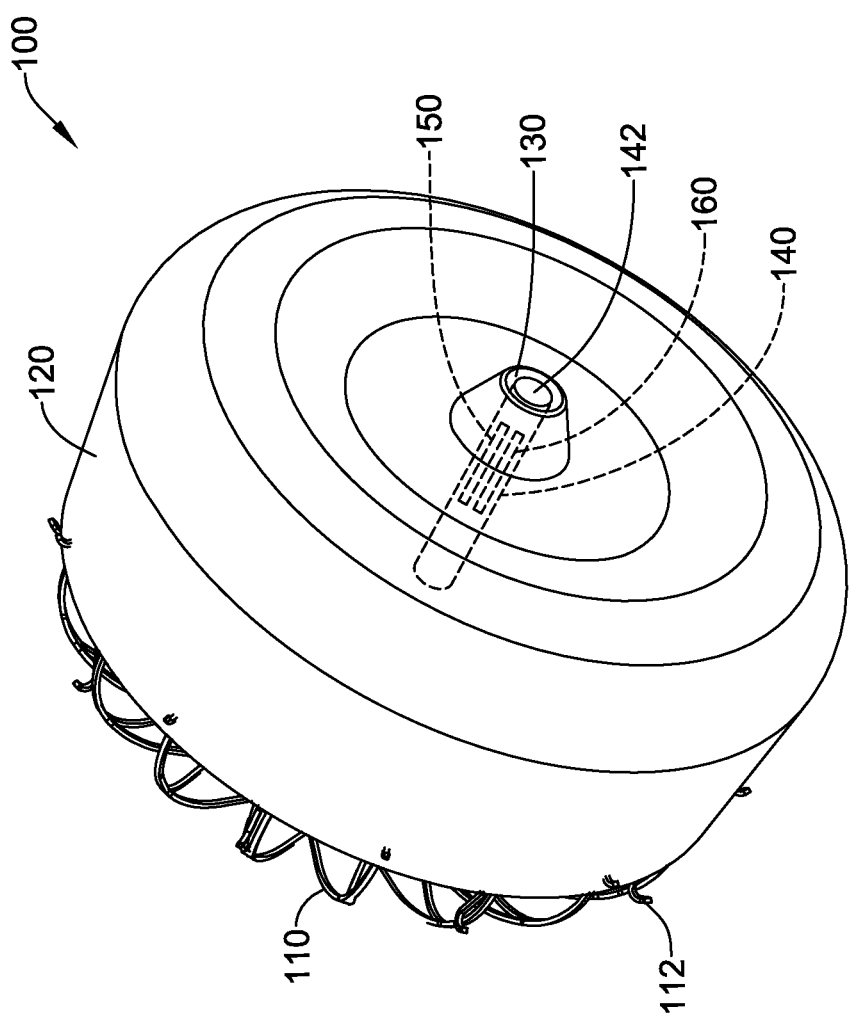
FIGS. 1-2 illustrate aspects of a left atrial appendage closure device.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the current disclosure. Those skilled in the art will recognize that the various elements described and/or shown may be arranged in various combinations and configurations without departing from the scope of the disclosure. The detailed description and drawings illustrate example embodiments of the current disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed example(s). Each instance of the features may include and/or be encompassed by the singular disclosure(s), unless expressly stated to the contrary. For simplicity and clarity purposes, not all elements of the current disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following figures illustrate selected components and/or arrangements of an implant for occluding the left atrial appendage, a medical system for occluding the left atrial appendage, and/or methods of using the implant and/or the medical system. It should be noted that in any given figure, some features may not be shown, or may be shown schematically, for simplicity. Additional details regarding some of the components of the implant and/or the system may be illustrated in other figures in greater detail. While discussed in the context of occluding the left atrial appendage, the implant and/or the system may also be used for other interventions and/or percutaneous medical procedures within a patient. Similarly, the devices and methods described herein with respect to percutaneous deployment may be used in other types of surgical procedures, as appropriate. For example, in some examples, the devices may be used in a non-percutaneous procedure. Devices and methods in accordance with the disclosure may also be adapted and configured for other uses within the anatomy.

Figure 2:
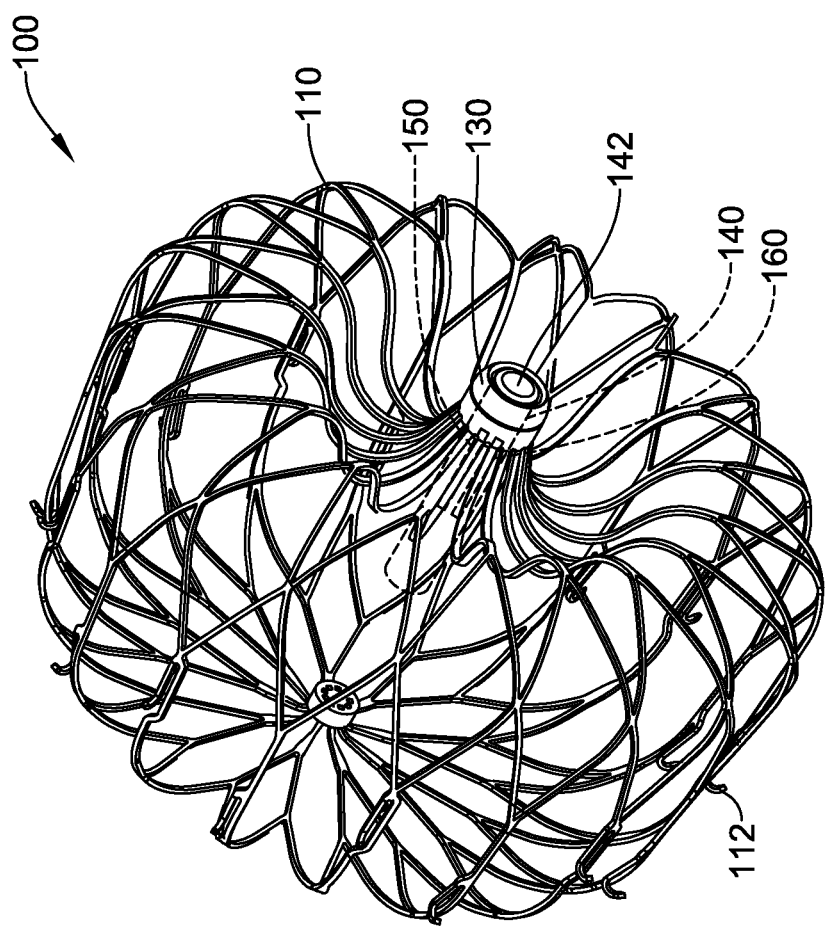

FIGS. 1-2 illustrate an example configuration of an implantable device 100 (e.g., a left atrial appendage closure device) comprising an expandable framework 110 configured to shift between a collapsed delivery configuration and an expanded deployed configuration. Hereinafter, the terms implantable device and left atrial appendage closure device may be considered to be interchangeable and may be used interchangeably throughout the disclosure. The implantable device 100 and/or the expandable framework 110 may be configured to shift between the collapsed delivery configuration and the expanded deployed configuration when the implantable device 100 is unconstrained. In the figures, the implantable device 100 is shown in the expanded deployed configuration. Some suitable, but non-limiting, examples of materials for the implantable device 100 and/or the expandable framework 110, etc. are discussed below.

In some embodiments, the implantable device 100 may include a proximal hub 130 centered on a central longitudinal axis of the expandable framework 110. For example, the proximal hub 130 may be coaxial with the central longitudinal axis of the expandable framework 110. In some embodiments, the proximal hub 130 may be configured to releasably attached the implantable device 100 and/or the expandable framework 110 to a delivery device (not shown) configured to deliver the implantable device 100 and/or the expandable framework 110 to the left atrial appendage of the patient. In some embodiments, the expandable framework 110 may include a plurality of interconnected struts joined together at the proximal hub 130. In some embodiments, the proximal hub 130 may be integrally formed with and/or may be monolithically formed with the expandable framework 110 and/or the plurality of interconnected struts. In some embodiments, the implantable device 100 may include, and/or the expandable framework 110 may be, a self-expanding framework.

In some embodiments, the implantable device 100 may optionally include an occlusive element 120 (e.g., a mesh, a fabric, a membrane, and/or other surface treatment) disposed on, disposed over, disposed about, or covering at least a portion of the expandable framework 110, as seen in FIG. 1. In some embodiments, the occlusive element 120 may be disposed on, disposed over, disposed about or cover at least a portion of an outer (or outwardly facing) surface of the expandable framework 110. In some embodiments, the occlusive element 120 may be secured to and/or may extend radially outward from the proximal hub 130. For reference, the occlusive element 120 has been removed from FIG. 2 to show selected aspects of the implantable device 100 otherwise hidden from view by the occlusive element 120.

In some embodiments, the expandable framework 110 may include a plurality of anchor members 112 disposed about a periphery of the expandable framework 110 in the expanded deployed configuration. The plurality of anchor members 112 may extend radially outward from the expandable framework 110. In some embodiments, the plurality of anchor members 112 may provide an anchoring mechanism to aid in retaining the implantable device 100 at a target site within a patient's anatomy (i.e., the left atrial appendage, for example) in the expanded deployed configuration. In some embodiments, the barb(s) may be configured, positioned, and/or arranged such that engagement of the barb(s) with surrounding tissue at the target site is minimized or avoided. In some embodiments, the barb(s) may not puncture, pierce, and/or extend into the surrounding tissue in the expanded deployed configuration.

In some embodiments, at least a portion of the occlusive element 120 may be secured to the expandable framework 110 by at least some of the plurality of anchor members 112. In at least some embodiments, at least a distal portion of the occlusive element 120 may be attached to the expandable framework 110. In some embodiments, at least some of the plurality of anchor members 112 extend and/or project through the occlusive element 120. In some embodiments, the occlusive element 120 may be attached to the expandable framework 110 at some and/or each of the plurality of anchor members 112, for example, by passing some and/or each of the plurality of anchor members 112 through the occlusive element 120.

In some embodiments, the barb and/or the tip portion on some and/or each of the at least some of the plurality of anchor members 112 may be disposed radially outward of the occlusive element 120 of the occlusive element 120 while the base of its respective anchor member is disposed radially inward of the occlusive element 120. The barb may serve to retain the occlusive element 120 on the expandable framework 110, thereby preventing the occlusive element 120 from working loose and/or releasing from the expandable framework 110 as the expandable framework 110 is shifted between the collapsed delivery configuration and the expanded deployed configuration. In some embodiments, attachment of the distal portion of the occlusive element 120 to the expandable framework 110 is devoid of sutures and/or adhesives.

In some embodiments, the occlusive element 120 may be permeable, semi-permeable, or impermeable to blood and/or other fluids, such as water. In some embodiments, the occlusive element 120 may include a polymeric membrane, a metallic or polymeric mesh, a porous filter-like material, or other suitable construction. In some embodiments, the occlusive element 120 may be configured to prevent thrombi (i.e. blood clots, etc.) from passing through the occlusive element 120 and/or exiting the left atrial appendage into the blood stream and/or the patient's circulatory system when the implantable device 100 and/or the expandable framework 110 is disposed within an ostium of the left atrial appendage in the expanded deployed configuration. In some embodiments, the occlusive element 120 may be configured to promote endothelization across the ostium of the left atrial appendage after implantation of the implantable device 100, thereby effectively removing the left atrial appendage from the patient's circulatory system. Some suitable, but non-limiting, examples of materials for the occlusive element 120 are discussed below.

In some embodiments, the implantable device 100 may include a first sensor 150 at least partially disposed within an interior of the expandable framework 110. The first sensor 150 may be secured to the expandable framework 110 and/or the proximal hub 130. The first sensor 150 may be configured to detect a first measurement. In some embodiments, the implantable device 100 may include a second sensor 160 at least partially disposed within an interior of the expandable framework 110. The second sensor 160 may be secured to the expandable framework 110 and/or the proximal hub 130. The second sensor may be configured to detect a second measurement. In some embodiments, the first sensor 150 and/or the second sensor 160 may be disposed within and/or may be contained within a sensor module 140. In some embodiments, each of the first sensor 150 and the second sensor 160 may be disposed and/or contained within its own sensor module.

In at least some embodiments, the sensor module 140, the first sensor 150, and/or the second sensor 160 may be at least partially disposed within the proximal hub 130, as seen in FIGS. 1 and 2. The first sensor 150 and/or the second sensor 160 may be in communication with a proximal end 142 of the sensor module 140. In some embodiments, the proximal end 142 of the sensor module 140 may be disposed substantially flush with a proximalmost extent of the proximal hub 130 in the released configuration. In some embodiments, the proximal end 142 of the sensor module 140 may extend proximal of the proximalmost extent of the proximal hub 130 in the released configuration. For example, in some embodiments, the proximal end 142 of the sensor module 140 may extend about 1 millimeter (mm), about 2 mm, about 3 mm, about 4 mm, about 5 mm, about 6 mm, about 7 mm, about 8 mm, or about 10 mm proximal of the proximalmost extent of the proximal hub 130 in the released configuration. In one example, the proximal end 142 of the sensor module 140 may extend about 4 mm to about 5 mm proximal of the proximalmost extent of the proximal hub 130 in the released configuration. Other ranges and/or dimensions are also contemplated. In some embodiments, the proximal end 142 of the sensor module 140 may have a convex shape extending in the proximal direction. In some embodiments having the proximal end 142 of the sensor module 140 with a convex shape, a proximalmost extent of the sensor module 140 may be substantially flush with the proximalmost extent of the proximal hub 130 in the released configuration. In some embodiments having the proximal end 142 of the sensor module 140 with a convex shape, the proximalmost extent of the sensor module 140 may extend proximal of the proximalmost extent of the proximal hub 130 in the released configuration.

In some embodiments, having the proximal end 142 of the sensor module 140 extend proximal of the proximalmost extent of the proximal hub 130 in the released configuration may permit endothelial growth over the occlusive element 120 and/or the ostium of the left atrial appendage without obstructing and/or obscuring the proximal end 142 of the sensor module 140. In some embodiments, the proximal end 142 of the sensor module 140 may be disposed distal of the proximalmost extent of the proximal hub 130 and proximal of a distal end of the proximal hub 130 in the released configuration such that the proximal end 142 of the sensor module 140 is recessed within the proximal hub 130 to permit and/or promote endothelial growth thereover. The skilled artisan will recognize that the type, construction, and capabilities of the sensor module 140 may be used to determine whether or not endothelial overgrowth should be permitted and/or promoted.

As shown in FIG. 2, the sensor module 140 may extend distally into the interior of the implantable device 100 and/or the expandable framework 110. In some embodiments, the sensor module 140 may have a substantially cylindrical outer surface. In some embodiments, the sensor module 140 may be hollow and/or may include an interior space configured to house components of the sensor module 140. An overall length of the sensor module 140 may vary depending on the construction of the sensor module 140 and/or components disposed within the interior space of the sensor module 140.

In one example configuration, the sensor module 140 may include one or more internal components disposed within the interior space. For example, the sensor module 140 may include the first sensor 150 and/or the second sensor 160 disposed therein. In some embodiments, any of the internal components may be considered optional in any particular example. In some embodiments, the first sensor 150 may be a pressure sensor. The first sensor 150 may be configured to sense a fluid pressure within a space facing the proximal end 142 of the sensor module 140 (e.g., a left atrium) and/or adjacent the proximal end 142 of the sensor module 140 when the expandable framework 110 and/or the implantable device 100 is disposed within an ostium of the left atrial appendage in the released configuration. Accordingly, the first measurement may be a left atrial pressure. In some embodiments, the second measurement may be a surrogate for the left atrial pressure. For example, the second measurement may be a third heart sound (S3). Additional details relating the third heart sound to the left atrial pressure are provided herein. In patients with physiological conditions where monitoring left atrial pressure may be beneficial, the same physiological conditions that may cause abnormal left atrial pressure may also cause and/or result in the third heart sound (S3). The third heart sound (S3) may be detected using the second sensor 160, which may have a different sensing modality than the first sensor 150. For example, the second sensor 160 may be an accelerometer, an acoustic sensor, or a pressure sensor sensitive to a particular frequency corresponding to the third heart sound (S3). Other sensor types are also contemplated. In some embodiments, the first sensor 150 may have a first sensing modality and may respond to a first set of daily physiological changes. The second sensor may have a second sensing modality and may respond to the same first set of daily physiological changes.

In some embodiments, the first sensor 150 and/or the second sensor 160 may be configured to sense and/or detect (and/or the sensor module 140 may include a sensor configured to sense and/or detect) temperature, flow rate, heart rate, electrical signals in the heart, heart rhythm, or other characteristics.

In some embodiments, the sensor module 140 may include an integrated circuit board for controlling the first sensor 150, the second sensor 160, and/or other internal components of the sensor module 140. In some embodiments, the sensor module 140 may include a communication coil disposed within the interior space of the sensor module 140. In some embodiments, the communication coil may be configured for bi-directional wireless communication and/or energy transfer. In some embodiments, the sensor module 140 may optionally include at least one battery. In some embodiments, the sensor module 140 may be powered "on-demand" via an inductive link. In some embodiments, the communication coil may be and/or may form a part of the inductive link. In some embodiments, the sensor module 140 may include at least one capacitor disposed within the interior space configured to act as a temporary power source for the sensor module 140, the first sensor 150, the second sensor 160, and/or other internal components of the sensor module 140 (during "on-demand" energy transfer to the sensor module 140 and/or the implantable device 100, for example). In some embodiments, the communication coil may be wrapped around the at least one battery. In some embodiments, the communication coil may be wrapped around the at least one capacitor. In some embodiments, the communication coil may be wrapped around a component containing a high permeability material (e.g. ferrite). In some embodiments, the communication coil may be a standalone feature and/or may be wrapped around an inert and/or non-functional structure to maintain shape and/or form. Other configurations are also contemplated.

In some embodiments utilizing the at least one battery, the at least one battery may be rechargeable. While a direct connection may be used to recharge the at least one battery, such a configuration may be rather invasive to the patient. Accordingly, a wireless (e.g., inductive) recharging capability may be more desirable and far less invasive to the patient. In some embodiments, utilizing the at least one battery, the at least one battery may not be rechargeable. When the at least one battery is non-rechargeable, it may be desirable to use at least one battery having a lifetime at least as long as the expected remaining lifetime of the patient to avoid needing to replace the at least one battery during a patient's later years when surgical procedures may be more challenging.

Figure 3:
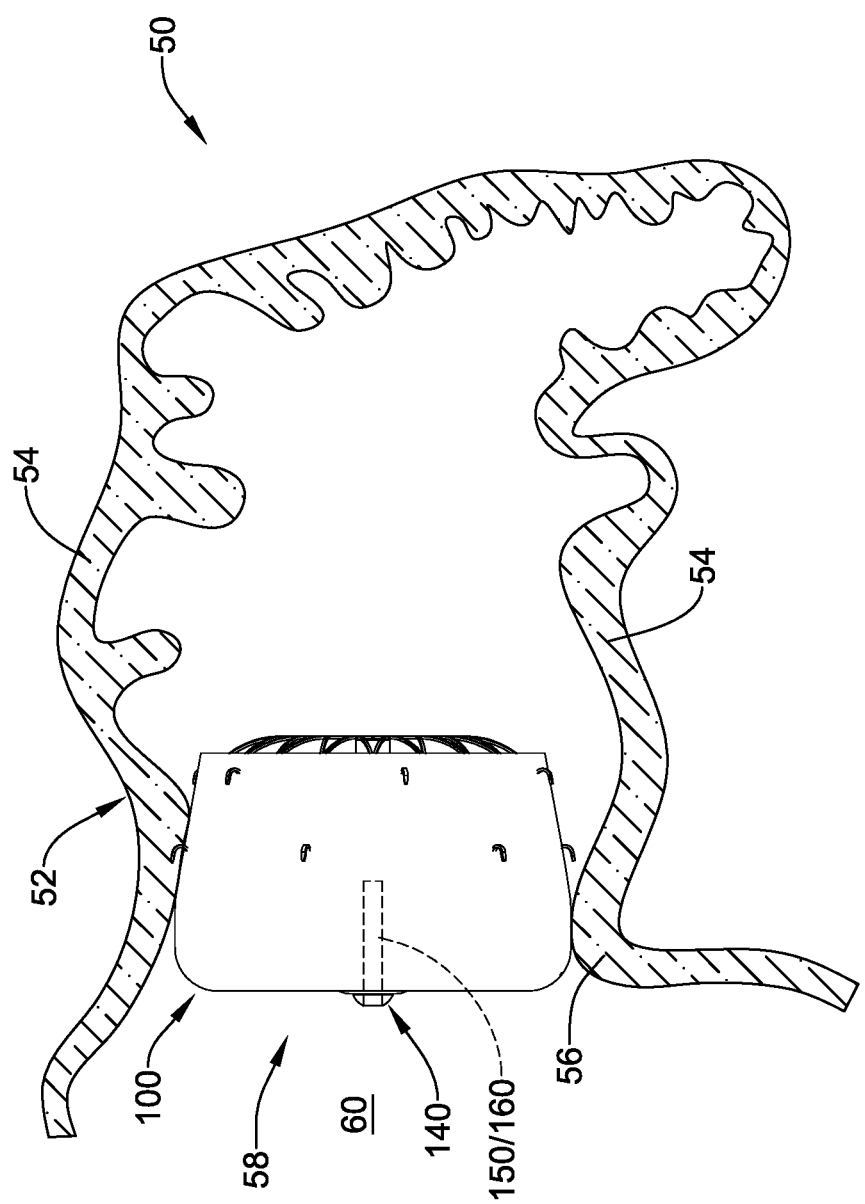
FIG. 3 illustrates the left atrial appendage closure device disposed within the ostium of a left atrial appendage of a heart of a patient.

FIG. 3 is a partial cross-sectional view of an example left atrial appendage 50, which may be attached to and in fluid communication with a left atrium 60 of a heart of a patient. In some patients, the left atrial appendage 50 may have a complex geometry and/or irregular surface area. Skilled artisans will recognize that the illustrated left atrial appendage is merely one of many possible shapes and sizes for the left atrial appendage 50, which may vary from patient to patient. Skilled artisans will also recognize that the medical devices, systems, and methods disclosed herein may be adapted for various sizes and shapes of the left atrial appendage 50, as necessary. The left atrial appendage 50 may include a generally longitudinal axis arranged along a depth of a main body 52 of the left atrial appendage 50. The main body 52 may include a wall 54 and an ostium 56 forming a proximal mouth 58. In some embodiments, a lateral extent of the ostium 56 and/or the wall 54 may be smaller or less than a depth of the main body 52 along the longitudinal axis, or a depth of the main body 52 may be greater than a lateral extent of the ostium 56 and/or the wall 54. In some embodiments, the left atrial appendage 50 may include a tail-like element associated with a distal portion of the main body 52, which element may protrude radially or laterally away from the main body 52.

As shown in FIG. 3, the implantable device 100 may be implanted within the ostium 56 of the left atrial appendage 50 to close off the proximal mouth 58 and substantially and/or completely sealing off the left atrial appendage 50 from the left atrium 60 and/or the patient's circulatory system. As noted herein, the sensor module 140 may face toward the left atrium 60 when implanted within the ostium 56 of the left atrial appendage 50. In at least some embodiments, the sensor module 140 may include a pressure sensor configured to sense fluid pressure within the left atrium 60 (e.g., left atrial pressure) when the implantable device 100 is disposed within the ostium 56 of the left atrial appendage 50 in the released configuration.

The expandable framework 110 may be compliant and substantially conform to and/or be in sealing engagement with the shape and/or geometry of the wall 54 and/or the ostium 56 of the left atrial appendage 50 in the expanded deployed configuration. In some embodiments, the implantable device 100 may expand to a size, extent, or shape less than or different from a maximum unconstrained extent, as determined by the surrounding tissue, the wall 54, and/or the ostium 56 of the left atrial appendage 50. In some embodiments, reducing a thickness of various elements of the expandable framework 110 may increase the flexibility and compliance of the expandable framework 110 and/or the implantable device 100, thereby permitting the expandable framework 110 and/or the implantable device 100 to conform to the tissue around it, rather than forcing the tissue to conform to the expandable framework 110 and/or the implantable device 100.

Figure 4:
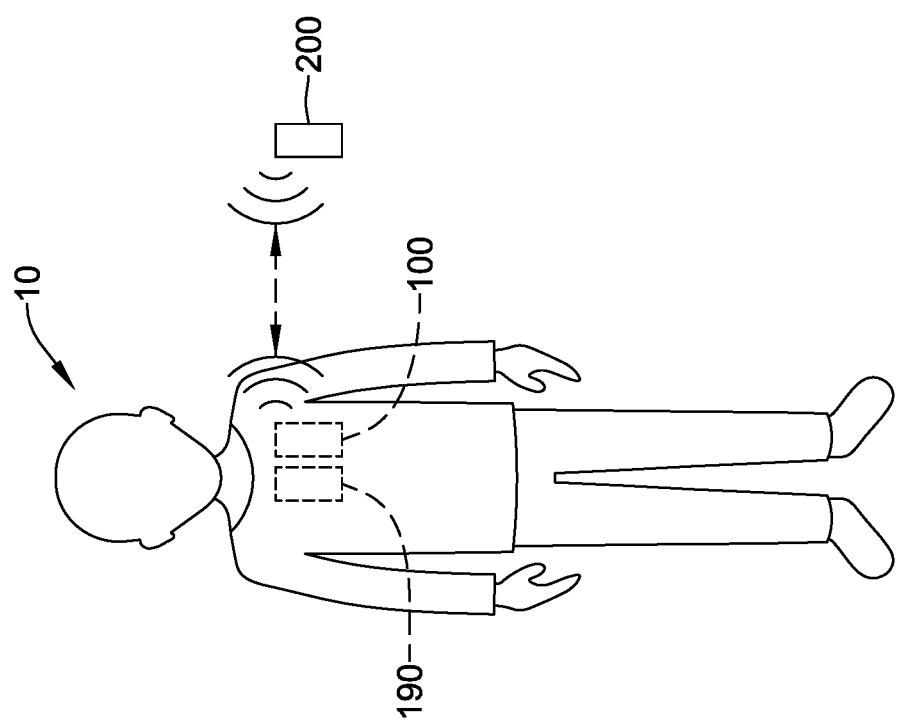
FIG. 4 illustrates aspects of a medical system for monitoring left atrial pressure in the heart of the patient.

FIG. 4 illustrates aspects of a medical system for monitoring a left atrial pressure within a heart of a patient. The medical system may include the implantable device 100, which may be implanted within the left atrial appendage 50 of the heart of the patient 10, and an external component 200 configured to communicate wirelessly with the implantable device 100. In some embodiments, the external component 200 may be a handheld device. In some embodiments, the external component 200 may be a portable device. In some embodiments, the external component 200 may be a user-worn device. In some embodiments, the external component 200 may be a fixed device (e.g., attached to a table, chair, or other fixture). In some embodiments, the external component 200 may be configured to communicate with a computer, a network, and/or a data storage unit. In some embodiments, the external component 200 may be configured to communicate with the computer, the network, and/or the data storage unit via a wired connection (e.g., ethernet, etc.). In some embodiments, the external component 200 may be configured to communicate with the computer, the network, and/or the data storage unit via a wireless connection (e.g., Wi-Fi, Bluetooth, near-field communication (NFC), etc.). In some embodiments, the external component 200 may include display capabilities including but not limited to built-in display screens, LEDs or indicator lights, analog dials, and/or meters or gauges. In some embodiments, the external component 200 may be connectable to an external display unit.

In some embodiments, the external component 200 may be configured to connect to an external power source (e.g., a wall outlet, a battery, etc.). In some embodiments, the external component 200 may include an internal power source (e.g., a battery, a capacitor, etc.). In some embodiments, the external component 200 may be configured to send and/or transmit power wirelessly to the implantable device 100 (e.g., via induction, etc.).

In some embodiments, at least one of the implantable device 100 and/or the external component 200 may include a processor configured to create a first trend for the first measurement, as discussed herein. The processor may be configured to use the first trend to modify the first measurement prior to outputting a corrected result. In some embodiments, the processor may be configured to create a second trend for the second measurement. In some embodiments, the processor may be configured to use the first trend and the second trend to modify the first measurement prior to outputting the corrected result. In some embodiments, the processor may be configured to use the first trend to remove drift from the first measurement prior to outputting the corrected result. In some embodiments, the processor may be configured to use the second trend to correct the first measurement for drift.

In an alternative configuration, the medical system may include a second medical device 190 configured to be in contact with a body of the patient 10. In some embodiments, the second medical device 190 may be a second implantable device. In some embodiments, the second medical device 190 may be disposed on and/or mounted to the skin of the patient. In some embodiments, the second medical device 190 may be a second external component. In some embodiments, the second medical device 190 may be a portable device and/or a handheld device. The second medical device 190 may be configured to communicate wirelessly with the implantable device 100 and/or the external component 200. In some embodiments, the second medical device 190 may include the second sensor 160. As such, the second medical device 190 may be configured and/or used to detect the second measurement when the second medical device 190 is in contact with the body of the patient 10.

Figure 5:
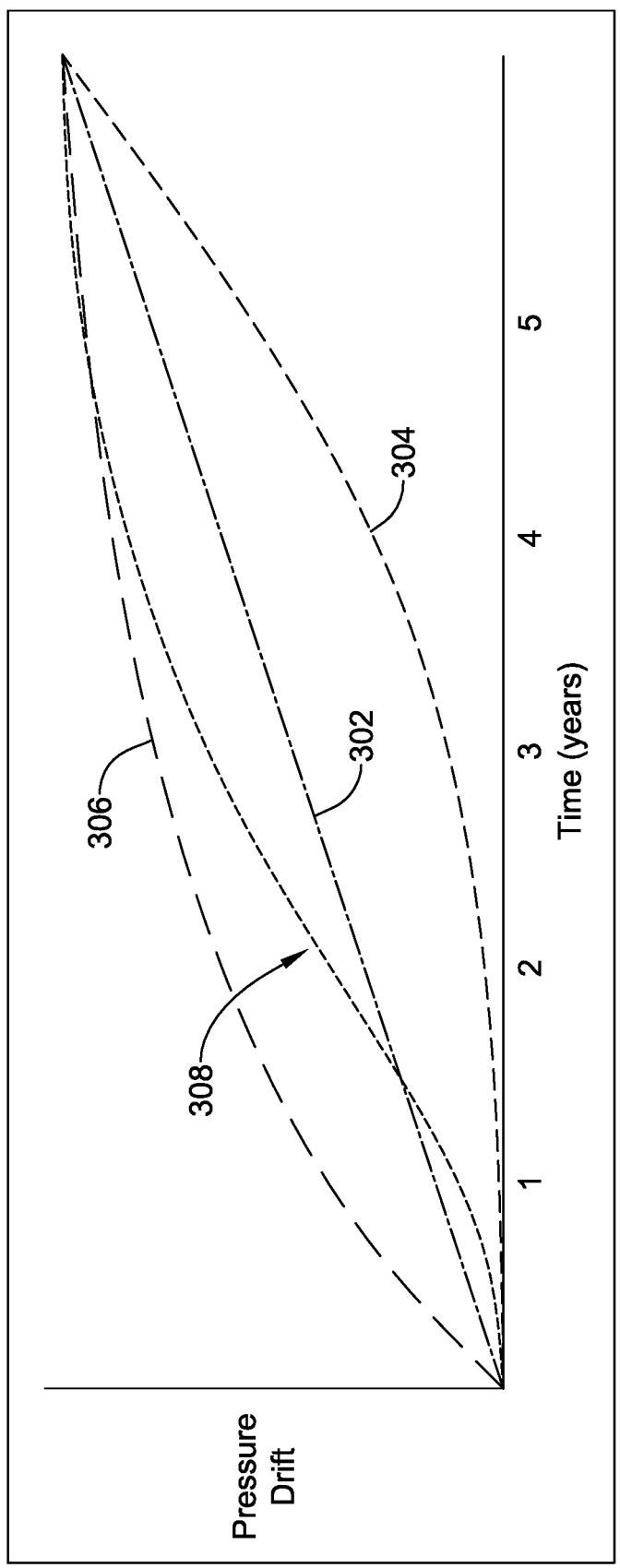
FIG. 5 illustrates example profiles of drift of a pressure sensor.

Pressure sensors can lose calibration over time due to one or more reasons. For example, sensor element aging and/or advancing physiological effects (such as tissue growth) may affect the calibration of the pressure sensor causing the pressure measurement to be less accurate. In some cases, sensor drift may be a slowly occurring phenomenon over the course of several months to years. As a result of this, the need for recalibration may not be apparent. Clinical action and/or treatments based on inaccurate pressure measurements may be a hazard to the patient. However, calibration drift generally occurs along a predictable profile, and the prediction may be made using and/or based on both pre-implant and post-implant data. FIG. 5 illustrates several different drift profiles that may identified and/or predicted. Generally speaking, the drift trend profile may be a linear trend 302, an exponential trend 304, a logarithmic trend 306, or a combination trend 308 combining two or more of these trends.

Figure 6:
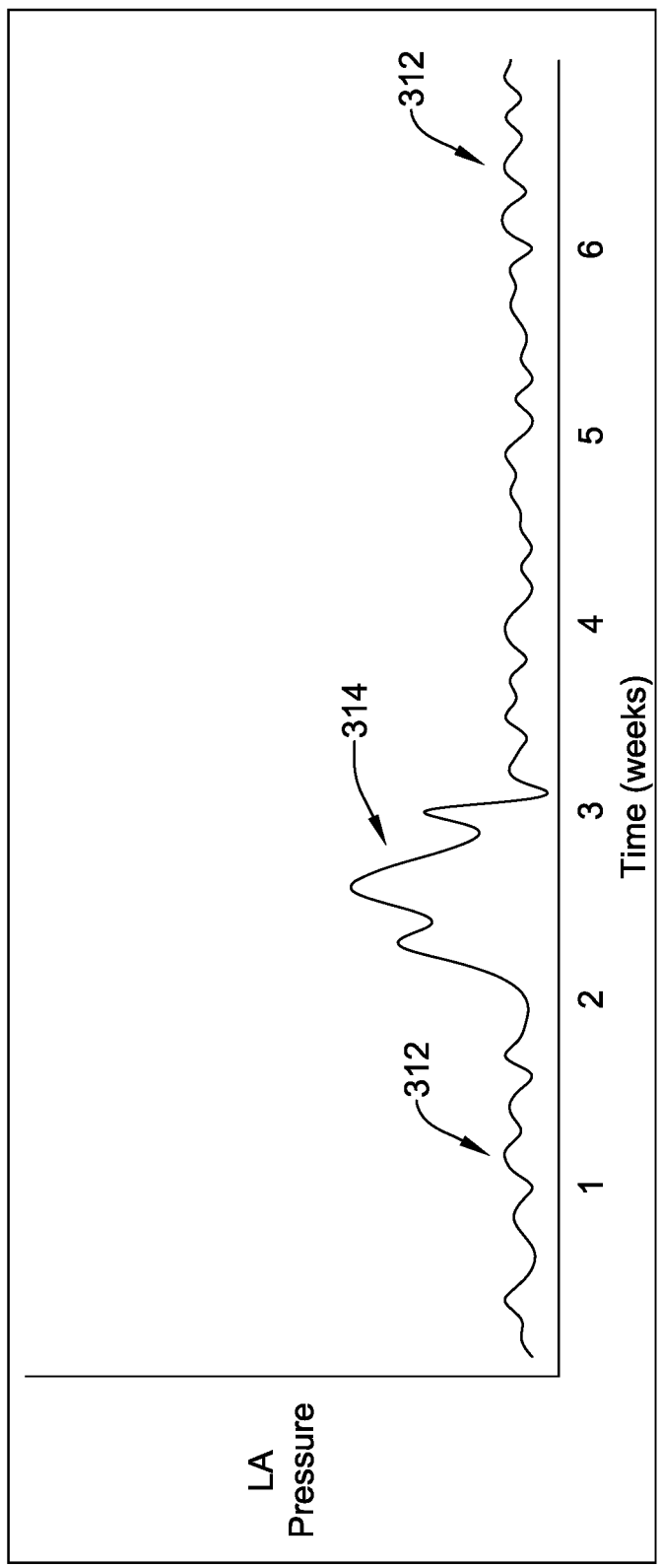
FIG. 6 illustrates an example left atrial pressure measurement using a pressure sensor.

Left atrial pressure changes due to most physiological events (e.g., heart failure, etc.) are irregular, which is related to nonpredictable events. As shown in FIG. 6, stable heart function may follow along a generally steady trend and/or within a reasonable and/or stable range illustrated at reference number 312. Even if the heart and/or the heart function is not necessarily healthy, the left atrial pressure will typically remain within the reasonable and/or stable range. However, left atrial pressure will be particularly elevated many days before a heart failure event. Thus, acute heart failure exacerbations or events, as shown at reference number 314, may be identifiable or predicted by measurements that are outside of the stable range indicated at reference number 312. It is noted that other physiological events (e.g., atrial fibrillation, valvular disease, etc.) may also affect left atrial pressure, and may in at least some instances be shown or manifested as a left atrial pressure exacerbation or event (e.g., reference number 314).

Figure 7A:
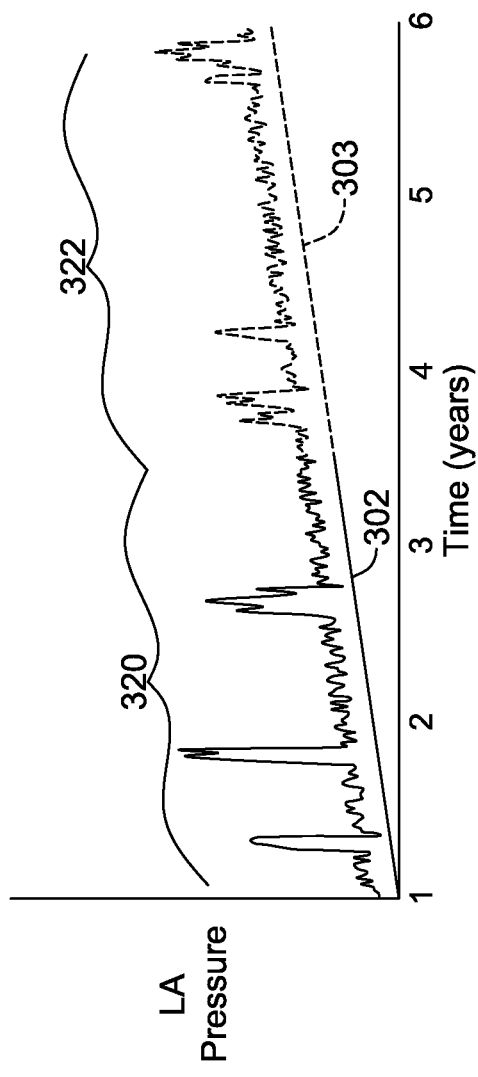
FIGS. 7A-7B illustrate example left atrial pressure measurements affected by drift.
Figure 7B:
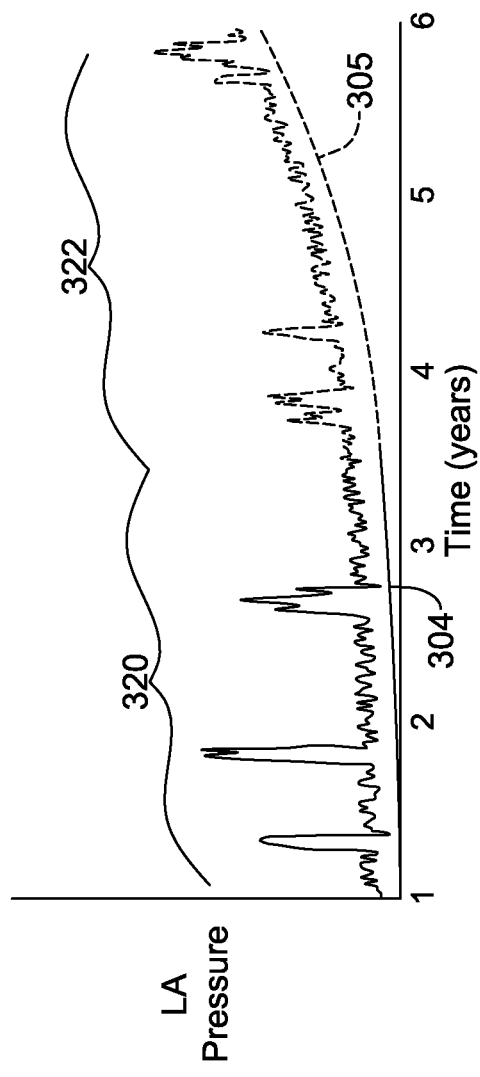

FIGS. 7A and 7B illustrate examples of the first measurement (e.g., left atrial pressure) charted over time to illustrate drift in the first sensor. The figures show the first measurement 320 and an associated drift trend profile. As shown in FIG. 7A, the first measurement 320 is slowly increasing over time, wherein the first measurement 320 is increasing along the linear trend 302. Using the actual data for the first measurement 320 and the linear trend 302, a predicted first measurement 322 may be identified along the expected and/or predicted linear trend 303 by extrapolating past sensor measurements and/or using pre-implant sensor characterization. Similarly, the first measurement 320 in FIG. 7B is increasing along the exponential trend 304. Again, using the actual data for the first measurement 320 and the exponential trend 304, a predicted first measurement 322 may be identified along the expected and/or predicted exponential trend 305 by extrapolating past sensor measurements and/or using pre-implant sensor characterization.

Figure 8:
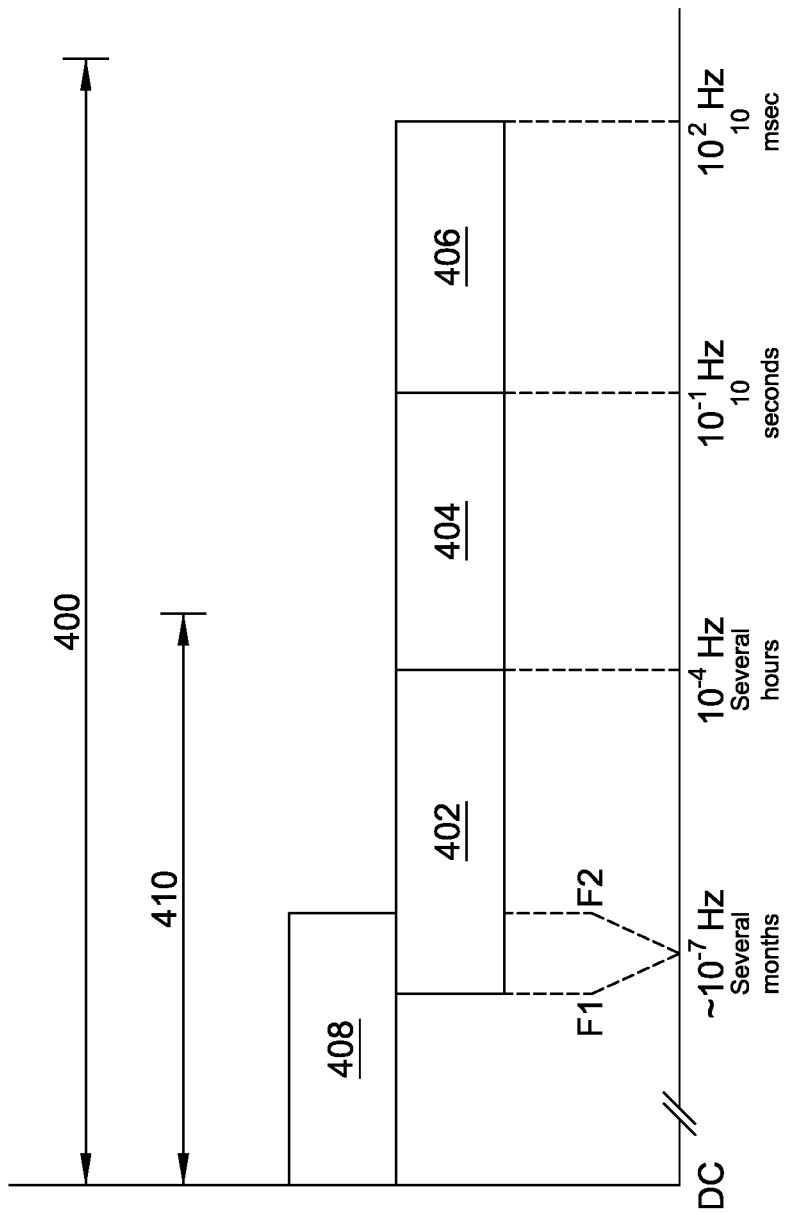
FIG. 8 illustrates example frequency ranges of a pressure signal.

FIG. 8 illustrates aspects or elements of the first measurement. As shown in FIG. 8, the first sensor 150 may detect a pressure signal 400 within a pressure sensor frequency range. As such, the pressure signal 400 may be used interchangeably with the first measurement. The pressure signal 400 and/or the pressure sensor frequency range may generally extend from a constant signal (DC) over a time scale of months or years to a frequency of about $10^2$ Hertz (Hz) over a time scale of milliseconds (msec). In some embodiments, the pressure signal 400 and/or the pressure sensor frequency range may extend to a frequency over $10^2$ Hz. Within the pressure signal 400 and/or the pressure sensor frequency range, there are two frequency bands of interest with respect to the left atrial pressure. The low frequency signal of interest 402 relates and/or corresponds to average filling pressure of the left ventricle and extends from about $10^{-7}$ Hz to about $10^{-4}$ Hz. The low frequency signal of interest 402 is slow and occurs over a relatively long period of time (e.g., days, weeks, months, years, etc.) and represented by for example the mean left atrial pressure per day. The high frequency signal of interest 406 relates and/or corresponds to cardiac and respiration morphology and extends from about $10^{-1}$ Hz to about $10^2$ Hz. The high frequency signal of interest 406 is faster and occurs over a relatively short period of time (e.g., seconds, fractions of second, within a single heartbeat, within a single respiratory cycle, etc.) and represented by the left atrial pressure real-time morphology. Between the low frequency signal of interest 402 and the high frequency signal of interest 406 is signal 404, extending from about $10^{-4}$ Hz to about $10^{-1}$ Hz. Signal 404 may be filtered out if there is substantial energy within it. Alternatively signal 404 may be ignored if its energy is low enough such that it does not interfere with measurement of the low frequency signal of interest 402 and the high frequency signal of interest 406.

The pressure signal 400 and/or the pressure sensor frequency range of the first sensor 150 may also include a drift value 408. The drift value 408 has very low frequency content extending from about $10^{-7}$ Hz down to DC. However, the lower edge F1 of the low frequency signal of interest 402 is not precisely known because it may vary due to characteristics of individual patients (no two patients are exactly the same). Additionally, the upper edge F2 of the drift value 408 are not precisely known because it is sensor dependent. In some embodiments, the lower edge F1 and the upper edge F2 may overlap (e.g., the low frequency signal of interest 402 may overlap the drift value 408), as shown in FIG. 8, the lower edge F1 and the upper edge F2 may abut at and/or share a common frequency (e.g., the low frequency signal of interest 402 may abut the drift value 408), or the lower edge F1 and the upper edge F2 may underlap or be spaced apart (e.g., there could be a frequency gap between the low frequency signal of interest 402 and the drift value 408).

As discussed herein, the second sensor 160 may be an accelerometer configured to detect a raw signal of the third heart sound (S3). The raw signal of the third heart sound (S3) may be used to produce, create, and/or determine an S3 signal 410, which may be measured periodically (e.g., weekly, daily, hourly, etc.) using the second sensor 160. The raw signal of the third heart sound (S3) may be comprised of frequencies between about 10 Hz and 50 Hz. An average amplitude of the above frequency contents of the raw signal of the third heart sound (S3) corresponds to how "loud" the raw signal of the third heart sound (S3) is and may be used to determine the S3 signal 410. The average amplitude of the S3 signal 410 has a frequency of about $10^{-4}$ Hz or less. The S3 signal 410 may generally extend from a constant signal (DC) over a time scale of months or years to a frequency of about $10^{-4}$ Hertz (Hz) over a time scale of hours. In some embodiments, the S3 signal 410 may extend to a frequency over $10^{-4}$ Hz. The S3 signal 410 is correlated to the low frequency signal of interest 402 from the first sensor 150, especially when left atrial pressure is elevated. As discussed herein, the same physiological conditions that cause elevated left atrial pressure also cause the third heart sound (S3). Therefore, as heart illnesses advance, the third heart sound (S3), which is generally not present or is undetectable in healthy patients, gets louder.

Figure 9:
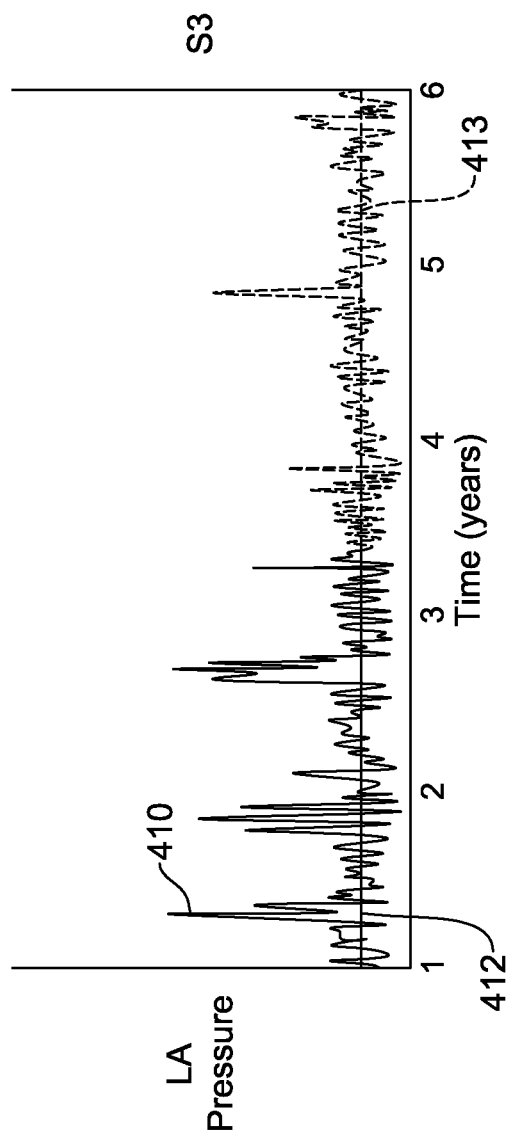
FIG. 9 illustrates an example left atrial pressure measurement using an accelerometer to monitor a third heart sound (S3)

However, the second sensor 160 and/or the accelerometer may be less accurate when used as a surrogate for left atrial pressure, because the second sensor 160 and/or the accelerometer may register larger spikes and/or valleys in the raw signal of the third heart sound (S3) than the first sensor 150 registers for the left atrial pressure, and/or the second sensor 160 and/or the accelerometer may register spikes when the left atrial pressure does not spike and the second sensor 160 and/or the accelerometer may fail to register spikes when the left atrial pressure does spike, as shown in FIG. 9. As such, the S3 signal 410 may exhibit greater variation in amplitude than the pressure signal from the first sensor 150. Comparing the graph of FIG. 9 to the graph of FIGS. 7A and 7B may further illustrate the less accurate nature of the S3 signal 410. One benefit of using the S3 signal 410 is that the S3 signal 410 may be inherently immune to the same type of drift experienced by the first sensor 150 (e.g., the pressure sensor). The second sensor 160 and/or the accelerometer may be used to detect the second measurement (e.g., the third heart sound (S3)) by detecting vibration and/or sound, and the value of the second measurement (e.g., the third heart sound (S3)) may be proportional to the intensity of the vibration and/or sound (e.g., the average amplitude).

The second measurement and/or the S3 signal 410 may be used to create a second trend 412, which may be and/or reflect a mean value for the S3 signal 410. The S3 signal 410 may correlate to the first measurement, the pressure signal 400, and/or the second trend 412 may correlate to the first trend (e.g., linear trend 302, exponential trend 304, etc.). Therefore, the second measurement and/or the S3 signal 410 may serve as a surrogate for the first measurement (e.g., the pressure signal 400). Additionally, using the actual data for the S3 signal 410 and the second trend 412, a predicted second trend 413 may be identified by extrapolating past sensor measurements and/or using pre-implant sensor characterization.

In some embodiments, the second trend 412 may be generally flat and/or constant, as shown in FIG. 9 for example, thus indicating that the second measurement and/or the S3 signal 410 contains no drift. The lack of drift in the second measurement makes the second measurement and/or the S3 signal 410 a good choice for verifying and/or correcting the first measurement for drift. However, the S3 signal 410 cannot capture the high frequency signal of interest 406 (e.g., FIG. 8) and may provide poorer prediction of heart function and/or possible heart failure. As such, the second measurement and/or the S3 signal 410 may not be a good standalone choice for detecting, measuring, and/or deriving left atrial pressure as a means to monitor heart function and/or to predict heart failure.

Figure 10:
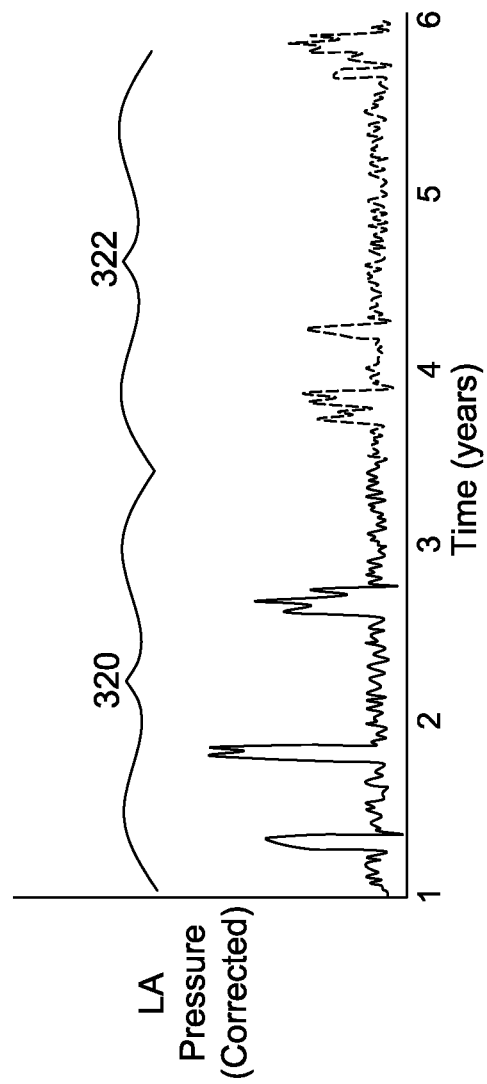
FIG. 10 illustrates the example left atrial pressure measurements of FIGS. 7A-7B corrected to remove drift.

In some embodiments, the second trend 412 may be angled or sloped (e.g., may not be flat or may not have a slope of zero). This does not indicate drift in the second measurement and/or the second sensor 160. Instead, as some physiological conditions advance and/or deteriorate, the first measurement and the second measurement may both trend in a similar direction (e.g., upward, downward, etc.). As such, in order to remove drift from the first measurement, a slope of the first trend may be compared to a slope of the second trend 412. Differences in slope between the first trend and the second trend 412 may illustrate and/or may equate to drift in the first measurement. Accordingly, the first trend and/or the second trend 412 may be used to modify the first measurement affected by drift (e.g., FIGS. 7A, 7B) to output a corrected result, shown in FIG. 10. For example, if the first trend is known, calculated, and/or predicted from past and/or current values/measurements, the first measurement may be modified using the first trend to produce the corrected result. In another example, if the second trend 412 is flat, the first trend may be simply removed from the first measurement to produce the corrected result. In still another example, if the first trend and the second trend 412 both slope in the same direction at the same value, physiological changes and/or deterioration can be assumed to be present, and no drift has occurred. In yet another example, if the first trend and the second trend 412 both slope in the same direction at different values, drift has occurred in the first measurement and/or the first sensor 150. In this example, the difference between the slope of the first trend and the slope of the second trend indicates and/or corresponds to drift. As such, the first measurement may be modified to remove the drift profile and/or to follow the slope of the second trend 412, thereby removing drift to produce and/or output the corrected result shown in FIG. 10, which more accurately reflects the true left atrial pressure.

Figure 11:
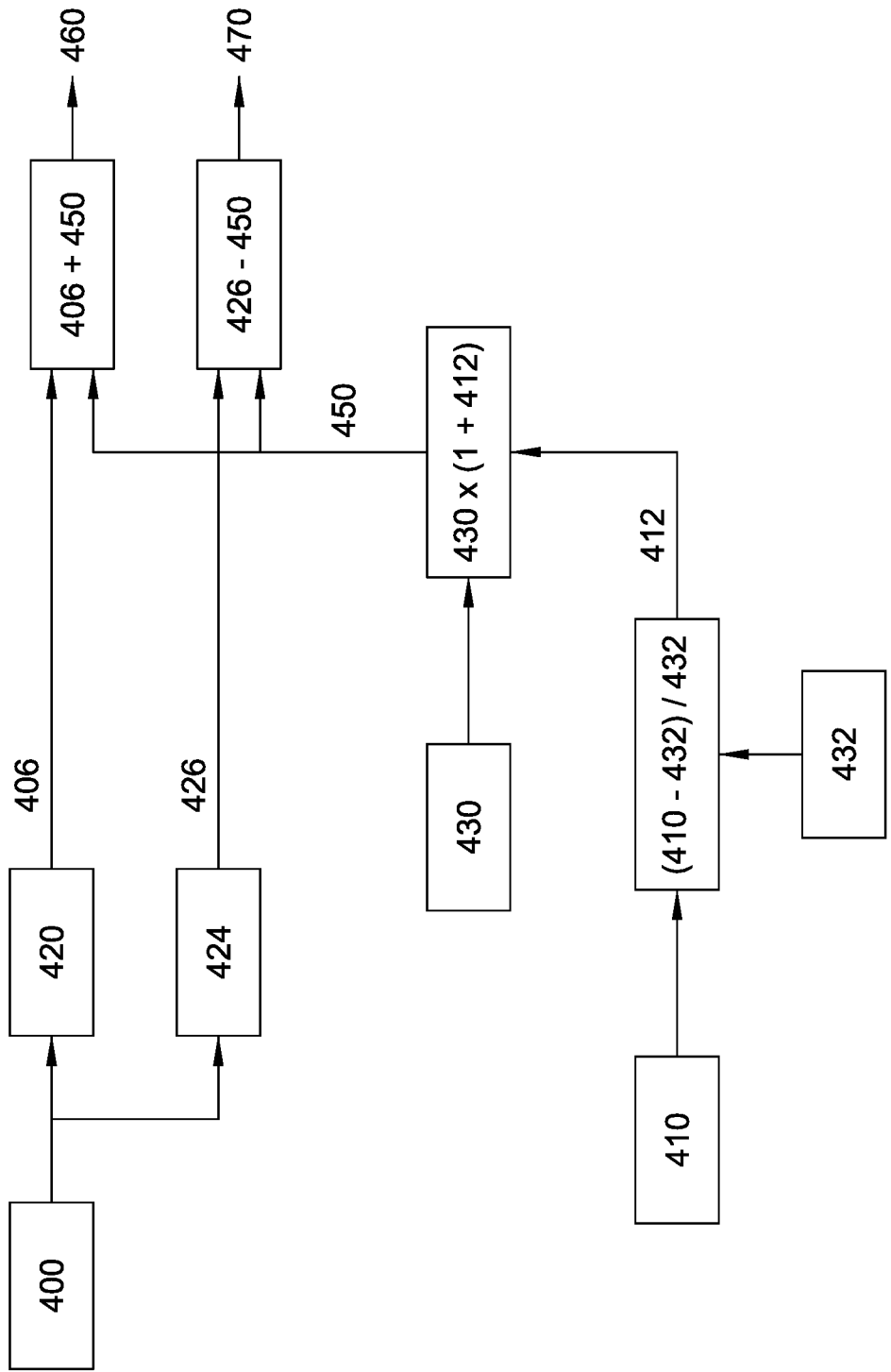
FIG. 11 illustrates example signal processing related to left atrial pressure.

FIG. 11 illustrates aspects of a method of autonomous recalibration of a pressure sensor used to detect the left atrial pressure within the heart of the patient. As discussed herein, the S3 signal 410 may be used to remove the drift value 408 (e.g., FIG. 8) and/or the first trend from the first measurement and/or the pressure signal 400. In some embodiments, the method may include detecting signals of the left atrial pressure (e.g., the first measurement and/or the pressure signal 400) using the first sensor 150 coupled to the expandable framework 110, the expandable framework 110 being implantable within the left atrial appendage 50 (e.g., FIG. 3) of the heart of the patient. During initial implantation of the implantable device 100, the first sensor 150 and/or the second sensor 160 may be calibrated and/or a calibration value may be saved within the relative sensor and/or the within the processor (or a data storage unit associated therewith). The calibration value of the first sensor 150 and/or the second sensor 160 may be used to establish the drift value and/or to determine a need for recalibration of the first sensor 150. The method may include using the signals of the left atrial pressure (e.g., the first measurement and/or the pressure signal 400) to establish a first trend of the left atrial pressure with the processor.

The method may include detecting signals of the third heart sound (S3) from the heart of the patient using the second sensor 160 coupled to the expandable framework 110. The method may include using the signals of the third heart sound (S3) to establish a second trend of the third heart sound (S3) with the processor. The method may further include comparing the first trend of the left atrial pressure to the second trend of the third heart sound (S3) with the processor to determine if the first sensor 150 is experiencing drift. The method may then use the second trend of the third heart sound (S3) to correct and/or modify the first trend of the left atrial pressure to remove the drift with the processor. The method may subsequently output a corrected trend and/or a correct first measurement of the left atrial pressure devoid of the drift.

In some embodiments, comparing the first trend of the left atrial pressure to the second trend of the third heart sound (S3) may include comparing the slope of the first trend of the left atrial pressure to the slope of the second trend of the third heart sound (S3). In some embodiments, using the second trend of the third heart sound (S3) to correct and/or modify the first trend of the left atrial pressure to remove the drift includes subtracting a difference between the slope of the second trend of the third heart sound (S3) and the slope of the first trend of the left atrial pressure from the first trend of the left atrial pressure. In some embodiments, when the drift exceeds a predetermined limit and/or when the slope of the first trend of the left atrial pressure exceeds the slope of the second trend of the third heart sound (S3) by a predetermined value, the method may further include issuing a warning (to and/or via the external component 200, for example) to manually recalibrate the first sensor 150.

In some embodiments, determining if the first sensor 150 is experiencing drift, and/or what the amount of drift is, takes place via signal processing within the processor. The first measurement and/or the pressure signal 400 may be separated into a low frequency pressure signal 426 (e.g., the low frequency signal of interest 402 plus the drift value 408) by a low pass filter 424 and the high frequency signal of interest 406 by a high pass filter 420. The second measurement and/or the S3 signal 410 may be compared to a stored S3 calibration value 432 for the second sensor 160 to determine the slope of the second trend 412 of the S3 signal 410. A stored pressure calibration value 430 for the first sensor 150 may then be modified by the slope of the second trend 412 of the S3 signal 410 to determine an expected low frequency pressure signal 450 (e.g., the low frequency signal of interest 402). The expected low frequency pressure signal 450 may then be used by the processor to determine a corrected left atrial pressure 460 and/or an actual drift value 470. In some embodiments, the actual drift value 470 may correspond to and/or may be the drift value 408 in the first measurement. The corrected left atrial pressure 460 may be determined by adding the high frequency signal of interest 406 and the expected low frequency pressure signal 450, as shown in FIG. 11. The actual drift value 470 may be determined by subtracting the expected low frequency pressure signal 450 from the low frequency pressure signal 426. In some embodiments, the actual drift value 470 may then be compared to the predetermined limit by the processor to determine if a warning should be issued to manually recalibrate the first sensor 150. As may be seen from the signal processing shown in FIG. 11, the high frequency signal of interest 406 does not drift. Drift is a gradual signal degradation that only presents itself within the low frequency signal of interest 402.

Figure 12:
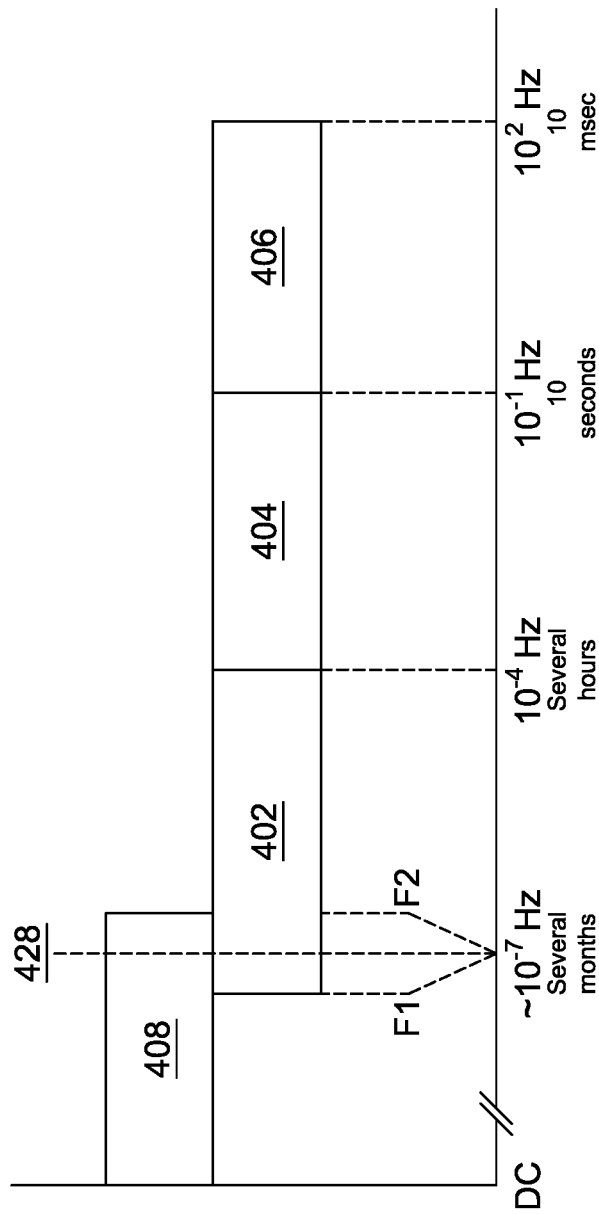
FIG. 12 illustrates example frequency ranges of a pressure signal and a filter.

In an alternative configuration, a method and medical system for monitoring the left atrial pressure in the heart of the patient may include using a signal filter having a signal cutoff frequency 428 of about $10^{-7}$ Hz, as shown in FIG. 12. In such a configuration, the medical system may include the implantable device 100 including the expandable framework 110 and the first sensor 150 secured to the expandable framework 110, and the external component 200 configured to communicate wirelessly with the implantable device 100. The first sensor 150 may be configured to detect the first measurement (e.g., the pressure signal 400). In at least some embodiments, the first sensor 150 may be a pressure sensor and the first measurement may be the left atrial pressure. The medical system may further include a processor and the signal filter. The signal filter may be used by the processor to modify the first measurement (e.g., the pressure signal 400) prior to outputting a corrected result (e.g., the corrected left atrial pressure 460).

Figure 13:
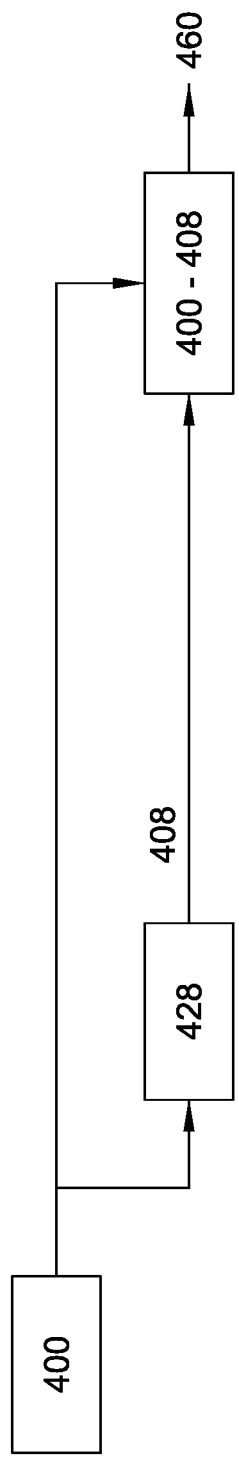
FIG. 13 illustrates example signal processing related to left atrial pressure using a low pass filter.

In some embodiments, the signal filter may be a low pass filter configured to create a signal representative of drift in the first measurement. The low pass filter only permits the drift value 408 of the pressure signal 400 (e.g., a portion of the pressure signal 400 below the cutoff frequency 428) to pass through. As such, the portion of the pressure signal 400 below the cutoff frequency 428 may be considered to be the signal representative of drift (e.g., the drift value 408) in the first measurement. The processor may be configured to subtract the signal representative of drift (e.g., the drift value 408) in the first measurement from the first measurement (e.g., the pressure signal 400) to produce the corrected result (e.g., the corrected left atrial pressure 460) devoid of drift, as shown in FIG. 13.

Figure 14:
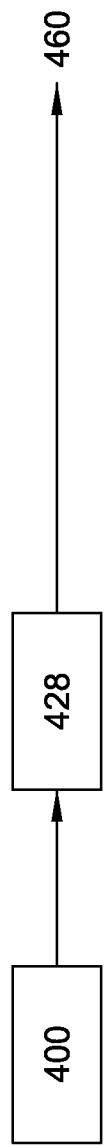
FIG. 14 illustrates example signal processing related to left atrial pressure using a high pass filter.

In some embodiments, the signal filter may be a high pass filter configured to remove a portion of the first measurement corresponding to drift (e.g., a portion of the pressure signal 400 below the cutoff frequency 428) in the first sensor 150 to produce the corrected result (e.g., the corrected left atrial pressure 460). The high pass filter only permits the portion of the pressure signal 400 above the cutoff frequency 428 to pass through. As such, the portion of the pressure signal 400 below the cutoff frequency 428, which consists primarily or entirely of drift, may be removed from the first measurement (e.g., the pressure signal 400) to produce the corrected result (e.g., the corrected left atrial pressure 460) devoid of drift, as shown in FIG. 14.

The materials that can be used for the various components of the medical system and the various elements thereof disclosed herein may include those commonly associated with medical devices. For simplicity purposes, the following discussion refers to the medical system. However, this is not intended to limit the devices and methods described herein, as the discussion may be applied to other elements, members, components, or devices disclosed herein, such as, but not limited to, the external component 200, the second medical device 190, the delivery device, the implantable device 100, the expandable framework 110, the occlusive element 120, the proximal hub 130, the sensor module 140, the first sensor 150, the second sensor 160, the signal filter, and/or elements or components thereof.

In some embodiments, the medical system and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly praraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In some embodiments, a linear elastic and/or non-superelastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the medical system and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical system in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical system to achieve the same result.

In some embodiments, a degree of Magnetic Resonance Imaging (MRI) compatibility is imparted into the medical system and/or other elements disclosed herein. For example, the medical system and/or components or portions thereof may be made of a material that does not substantially distort the image and create substantial artifacts (i.e., gaps in the image). Certain ferromagnetic materials, for example, may not be suitable because they may create artifacts in an MRI image. The medical system or portions thereof may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the medical system and/or other elements disclosed herein may include a fabric material disposed over or within the structure. The fabric material may be composed of a biocompatible material, such as a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the medical system and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the medical system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A method of autonomous recalibration of a pressure sensor used to detect a left atrial pressure within a heart of a patient, comprising:

detecting signals of the left atrial pressure using a first sensor coupled to an expandable framework, the expandable framework being implantable within a left atrial appendage of the heart of the patient;

detecting signals of a third heart sound (S3) from the heart of the patient using a second sensor coupled to the expandable framework;

using the signals of the left atrial pressure to establish a trend of the left atrial pressure with a processor;

using the signals of the third heart sound to establish a trend of the third heart sound with the processor;

comparing the trend of the left atrial pressure to the trend of the third heart sound with the processor to determine if the first sensor is experiencing drift, including comparing a slope of the trend of the left atrial pressure to a slope of the trend of the third heart sound; and using the trend of the third heart sound to correct the trend of the left atrial pressure to remove the drift with the processor;

outputting a corrected trend of the left atrial pressure devoid of the drift.

2. The method of claim 1, wherein using the trend of the third heart sound to correct the trend of the left atrial pressure to remove the drift includes subtracting a difference between the slope of the trend of the third heart sound and the slope of the trend of the left atrial pressure from the trend of the left atrial pressure.

3. The method of claim 1, wherein when the drift exceeds a predetermined limit, the method further includes issuing a warning to manually recalibrate the first sensor.

4. The method of claim 1, wherein the first sensor has a first sensing modality and responds to a first set of daily physiological changes of the heart, and the second sensor has a second sensing modality different from the first sensing modality and responds to the first set of daily physiological changes of the heart.

* * * * *